United States Patent
Marvi et al.

(10) Patent No.: US 11,534,255 B2
(45) Date of Patent: Dec. 27, 2022

(54) SYSTEMS AND METHODS FOR CONTROLLING SHAPE AND POSITION OF A FERROFLUID DROPLET

(71) Applicant: Arizona Board of Regents on behalf of Arizona State University, Tempe, AZ (US)

(72) Inventors: Hamidreza Marvi, Chandler, AZ (US); Mahdi Ilami, Tempe, AZ (US); Reza James Ahmed, Tempe, AZ (US)

(73) Assignee: Arizona Board of Regents on Behalf of Arizona State University, Tempe, AZ (US)

( * ) Notice: Subject to any disclaimer, the term of this patent is extended or adjusted under 35 U.S.C. 154(b) by 0 days.

(21) Appl. No.: 17/638,125

(22) PCT Filed: Aug. 26, 2020

(86) PCT No.: PCT/US2020/047892
§ 371 (c)(1),
(2) Date: Feb. 24, 2022

(87) PCT Pub. No.: WO2021/041471
PCT Pub. Date: Mar. 4, 2021

(65) Prior Publication Data
US 2022/0265379 A1 Aug. 25, 2022

Related U.S. Application Data

(60) Provisional application No. 62/892,052, filed on Aug. 27, 2019.

(51) Int. Cl.
*A61B 34/00* (2016.01)
*H02N 15/00* (2006.01)
*B82Y 25/00* (2011.01)

(52) U.S. Cl.
CPC .............. *A61B 34/73* (2016.02); *B82Y 25/00* (2013.01); *H02N 15/00* (2013.01); *A61B 2034/731* (2016.02)

(58) Field of Classification Search
CPC ... A61B 34/73; A61B 2034/731; B82Y 25/00; H02N 15/00
See application file for complete search history.

(56) References Cited

U.S. PATENT DOCUMENTS 8,888,674 B2   11/2014   Shapiro et al.
9,733,168 B2   8/2017    Miller et al.

OTHER PUBLICATIONS

International Search Report and Written Opinion issued in corresponding Application No. PCT/US2020/047892 dated Nov. 20, 2020, 9 pages.
Zhu et al., Nonlinear deformation of a ferrofluid droplet in a uniform magnetic field, Langmuir 27.24 (2011) 14834-14841. [online] <url:https://pubs.acs.org/doi/abs/10.1021/la203931q> <doi:10.1021/la203931q>.

(Continued)

*Primary Examiner* — Mohamad A Musleh
(74) *Attorney, Agent, or Firm* — Polsinelli PC

(57) ABSTRACT

Various embodiments of a system and method for controlling the shape, subdivision, recombination, movement and object manipulation of ferrofluid material in addition to pumping fluids with ferrofluid material using external electromagnetic fields are disclosed herein.

21 Claims, 12 Drawing Sheets

(56) References Cited

OTHER PUBLICATIONS

Nacev et al., Towards control of magnetic fluids in patients: directing therapeutic nanoparticles to disease locations, IEEE Control Systems Magazine 32.3 (2012) 32-74 (included pp. 32-36, 43-47) [online] <url:http://www.controlofmems.umd.edu/publications/joural-papers/2012/NacevEtAl-MagControl-wFig6aFixed_authors-Sep2012-21MB.pdf> <doi: 10.1109/MCS.2012.2189052>.
Leon-Rodriguez et al., Ferrofluid soft-robot bio-inspired by Amoeba locomotion 2015 15th International Conference on Control, Automation and Systems (ICCAS), IEEE, 2015. [online] <url:https://ieeexplore.ieee.org/abstract/document/7364657> <doi:10.1109/ICCAS.2015.7364657>.
Burgner-Kahrs J, Rocker DC, Choset H. Continuum robots for medical applications: A survey. IEEE Transactions on Robotics. 2015;31(6):1261-1280.
Ilami M, Ahmed RJ, Petras A, et al. Magnetic needle steering in soft phantom tissue. Scientific reports. 2020;10(1):1-11.
Nelson BJ, Kaliakatsos IK, Abbott JJ. Micro-robots for minimally invasive medicine. Annu Rev Biomed Eng. 2010;12(1):55-85.
Bogue R, Troccaz J. The development of medical microrobots: a review of progress. Ind Rob. 2008; 35(4):294-299.
Kummer MP, Abbott JJ, Kratochvil BE, et al. Octomag: An electromagnetic system for 5-dof wire-less micromanipulation. IEEE Trans Robot. 2010; 26(6): 1006-1017.
Hajba L, Guttman A. Circulating tumor-cell detection and capture using microfluidic devices. Trends Analyt Chem. 2014;59:9-16.
Steager EB, Sakar MS, Magee C, et al. Automated biomanipulation of single cells using magnetic mi-crorobots. Int J Rob Res. 2013;32(3):346-359.
Onoda M, Ueki T, Tamate R, et al. Amoeba-like self-oscillating polymeric fluids with autonomous sol-gel transition. Nat Commun. 2017;8:15862.
Fusco S, Huang HW, Peyer KE, et al. Shape-switching microrobots for medical applications: The influence of shape in drug delivery and locomotion. ACS Appl Mater Interfaces. 2015;7(12):6803¬6811.
Huang HW, Sakar MS, Petruska AJ, et al. Soft micromachines with programmable motility and morphology. Nat Common. 2016;7:12263.
Dreyfus R. An attractive, reshapable material. Science. 2019;365(6450):219-219.
Liu X, Kent N, Ceballos A, et al. Reconfigurable ferromagnetic liquid droplets. Science. 2019; 365(6450):264-267.
Huang G, Li M, Yang Q, et al. Magnetically actuated droplet manipulation and its potential biomedical applications. ACS Appl Mater Interfaces. 2017;9(2):1155-1166.
Ilami M, Ahmed RJ, Edwards D, et al. Magnetically actuated tunable soft electronics. ACS omega. 2019.
Komaee A, Shapiro B. Steering a ferromagnetic particle by magnetic feedback control: Algorithm design and validation. In: Proceedings of the 2010 American Control Conference. 2010; 6543-6548.
Probst R, Lin J, Komaee A, et al. Planar steering of a single ferrofluid drop by optimal minimum power dynamic feedback control of four electro-magnets at a distance. J Magn Magn Mater. 2011; 323(7):885-896.
Ody T, Panth M, Sommers AD, et al. Controlling the motion of ferrofluid droplets using surface tension gradients and magnetoviscous pinning. Lang-muir. 2016; 32(27):6967-6976.
Katsikis G, Breant A, Rinberg A, et al. Synchronous magnetic control of water droplets in bulk ferrofluid. Soft Matter. 2018;14:681-692.
Jamin T, Py C, Falcon E. Instability of the origami of a ferrofluid drop in a magnetic field. Phys Rev Lett. 2011;107:204503.
Anjos PHA, Carvalho GD, Lira SA, et al. Wrinkling and folding patterns in a confined ferrofluid droplet with an elastic interface. Phys Rev E. 2019; 99:022608.
Varma VB, Ray A, Wang Z, et al. Control of ferrofluid droplets in microchannels by uniform magnetic fields. IEEE Magn Lett. 2016;7:1-5.
Chen CY, Hsueh HC, Wang SY, et al. Self-assembly and novel planetary motion of ferrofluid drops in a rotational magnetic field. Microfluid Nanofluidics. 2014;18.
Cunha LHP, Siqueira IR, Oliveira TF, et al. Field-induced control of ferrofluid emulsion rheology and droplet break-up in shear flows. Phys Fluids. 2018; 30(12):122110.
Zhu GP, Nguyen NT, Ramanujan RV, et al. Non-linear deformation of a ferrofluid droplet in a uniform magnetic field. Langmuir. 2011;27(24):14834-14841.
Ghaffari A, Hashemabadi SH, Bazmi M. Cfd simulation of equilibrium shape and coalescence of ferrofluid droplets subjected to uniform magnetic field. Colloids Surf A Physicochem Eng Asp. 2015; 481:186-198.
Afkhami S, Tyler AJ, Renardy Y, et al. Deformation of a hydrophobic ferrofluid droplet suspended in a viscous medium under uniform magnetic fields. J Fluid Mech. 2010;663:358-384.
Ghaffari A, Hashemabadi SH. Parameter study and CFD analysis of head on collision and dynamic behavior of two colliding ferrofluid droplets. Smart Mater Struct. 2017;26(3):035010.
Qian J, Law CK. Regimes of coalescence and separation in droplet collision. J Fluid Mech. 1997; 331:59-80.
Rosensweig, RE. Ferrohydrodynamics. Dover Books on Physics. Dover Publications. 2013.
Mika Latikka and Matilda Backholm and Jaakko VI Timonen and Robin HA Ras. Wetting of ferrofluids: Phenomena and control. Current Opinion in Colloid & Interface Science. 2018; 36:118-129. Wetting and Spreading.
Kawun P, Leahy S, Lai Y. A thin pdms nozzle/diffuser micropump for biomedical applications. Sens Actuators A Phys. 2016;249:149-154.
Afkhami S, Renardy Y, Renardy M, et al. Field-induced motion of ferrofluid droplets through immiscible viscous media. J Fluid Mech. 2008; 610:363-380.
Afkhami S, Renardy Y, Renardy M, et al. Numerical modeling of ferrofluid droplets in magnetic fields. AIP Conf Proc. 2008;1027(1):884-886.
Canny J. A computational approach to edge detection. IEEE Trans Pattern Anal Mach Intell. 1986; 8(6):679-698.

200

202 Using feedback from an image processing module, determine an error between desired properties and instant properties of a ferrofluidic robot $$e_L = L_d - L$$
$$e_\theta = \theta_d - \theta$$
$$E_P = P_d - P$$

204 Determine stretch length, stretch angle and force to be applied to the ferrofluidic robot using respective controllers $e_L$ -> Stretch Length Controller -> $L_B$
$e_\theta$ -> Stretch Angle Controller -> $\theta_B$
$E_P$ -> Position Controller -> $F_G$

206 Identify a set of currents to be applied to each respective electromagnetic coil to achieve desired results based on $L_B$, $\theta_B$ and $F_G$ $$I = A_{B,F}(\mathbf{M}, \mathbf{P})^\dagger \begin{bmatrix} \mathbf{B}_{\text{desired}} \\ \mathbf{F}_{\text{desired}} \end{bmatrix}$$

208 Generate feedback by identifying instant parameters of the ferrofluid robot using the image processing module and a camera oriented towards the ferrofluid robot $L, \theta, \mathbf{P} = (P_X; P_Y)$

FIG. 2

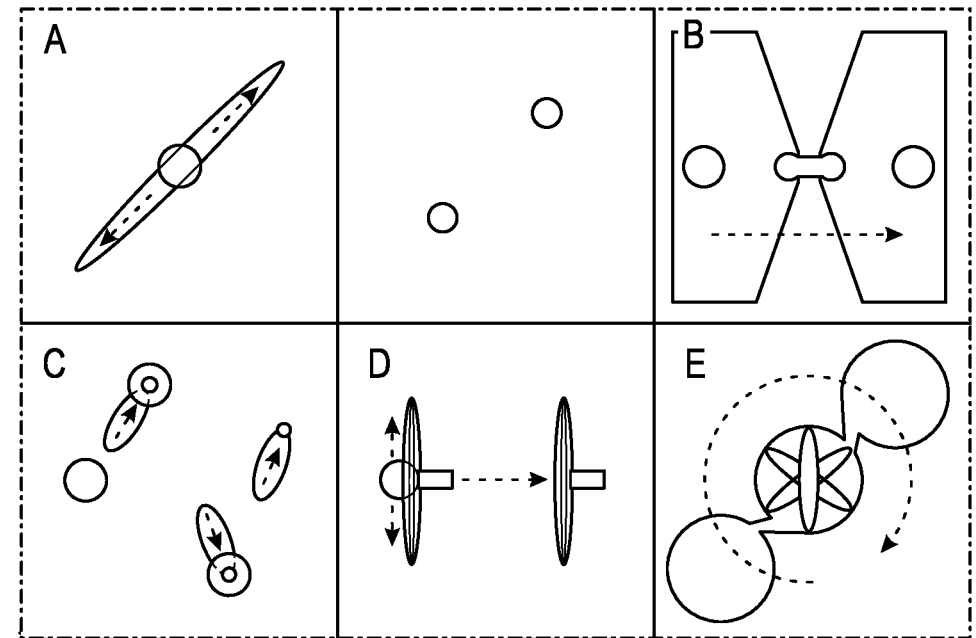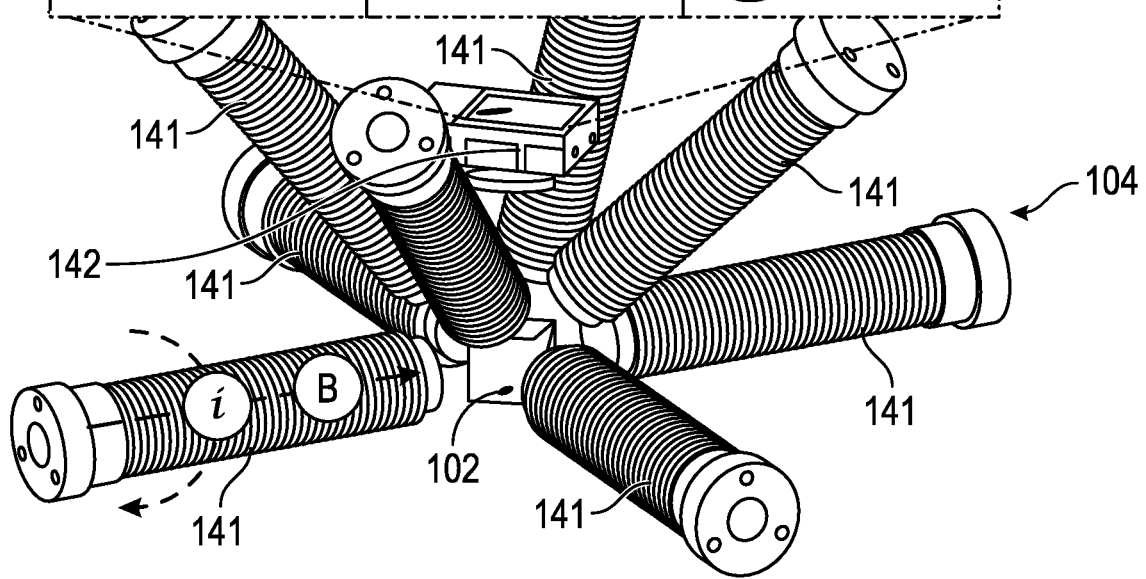
FIG. 3

SYSTEMS AND METHODS FOR CONTROLLING SHAPE AND POSITION OF A FERROFLUID DROPLET

CROSS-REFERENCE TO RELATED APPLICATIONS

This application claims priority to U.S. Provisional patent application No. 62/892,052 filed Aug. 27, 2019, which is herein incorporated by reference in its entirety.

FIELD

The present disclosure generally relates to the control of ferrofluid; and in particular, to systems and methods for controlling the shape, subdivision, engulfment, movement and object manipulation of ferrofluid material using external magnetic fields.

BACKGROUND

Medical robotic technology is striving towards less invasive operations and procedures in order to benefit patients and provide shorter recovery times and decreased risk of infection or complication. Many current bio-inspired micro- and nano-robotic technologies are limited in speed, means, and direction of motion or position, practical fabrication, or the ability to deform and reform. Ferrofluid, a stable colloidal suspension of small magnetic particles, is a promising material that has the potential to mimic some bio-inspired properties of amoebas and other small organisms; however, previous technologies have yet to master the control of ferrofluid, particularly the simultaneous shape and position control of ferrofluid.

It is with these observations in mind, among others, that various aspects of the present disclosure were conceived and developed.

BRIEF DESCRIPTION OF THE DRAWINGS

FIG. 2 is a flowchart illustrating a method for control of the ferrofluid droplet using the system of FIG. 1A;

FIG. 3 is a diagram showing conceptualization of the ferrofluid droplet control system in the form of five functional maneuvers: splitting into two separate parts, squeezing through a small channel, engulfment and transport of wettable particles, pushing/manipulating non-wettable particles, and pumping/flow manipulation in a fluidic channel;

Corresponding reference characters indicate corresponding elements among the view of the drawings. The headings used in the figures do not limit the scope of the claims.

SUMMARY

Figure 1:
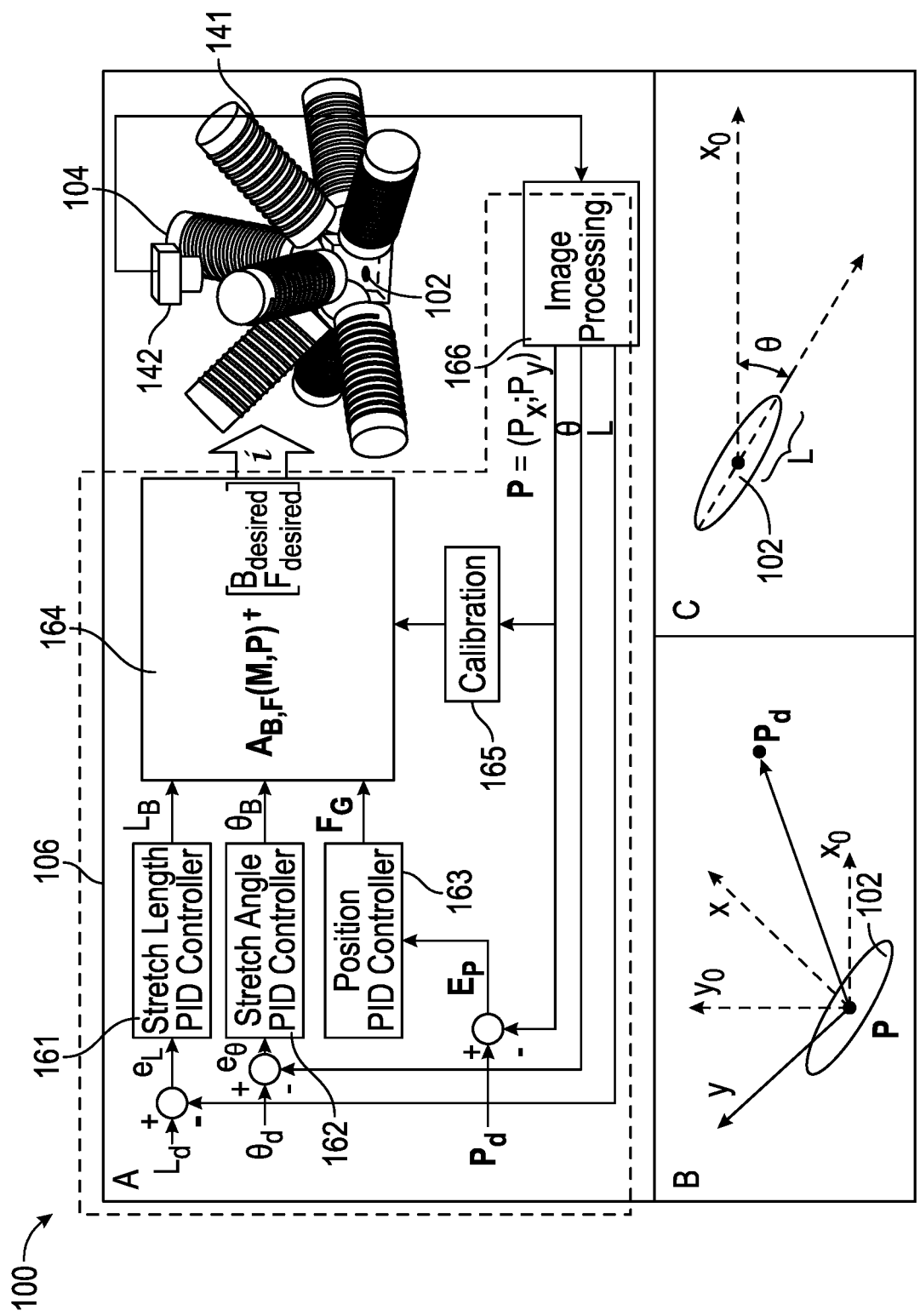
FIGS. 1A-1C are respective diagrams illustrating a system for control of a ferrofluid droplet including a control mechanism, an electromagnetic field generation system, and a ferrofluid droplet (FIG. 1A), a definition of position control parameters for a ferrofluid droplet illustrated as a vector error between current robot position and a desired position (FIG. 1B), and a definition of shape control parameters (stretch angle and stretch length) of the ferrofluid droplet (FIG. 1C)

Aspects of the present disclosure provide a system 100 for the control of a ferrofluid droplet 102, the system 100 comprising a ferrofluid droplet 102 and an electromagnetic field generation system 104, the electromagnetic field generation system 104 comprising a plurality of electromagnetic coils 141, the plurality of electromagnetic coils 141 being operable to generate a magnetic field B when an electric current i is applied to each of the plurality of coils 141. The system 100 further includes a controller 106 in operative communication with the electromagnetic field generation system 104 for storing instructions, which, when executed, cause the controller 104 to determine an instant position P, an instant stretch angle θ and an instant stretch length L of the ferrofluid droplet 102, identify a position difference Ep between instant position P and a target position $P_d$, a stretch angle difference ee between instant stretch angle θ and a target stretch angle $θ_d$, and a stretch length difference $e_L$ between instant stretch length L and a target stretch length $L_d$, determine a magnetic field magnitude $L_B$ necessary to manipulate the ferrofluid droplet 102 into the target stretch length $L_d$ from the instant stretch length L, a magnetic field angle $θ_B$ necessary to manipulate the ferrofluid droplet 102 into the target stretch angle $θ_d$ from the instant stretch angle θ, and a force vector $F_G$ necessary to manipulate the ferrofluid droplet 102 into the target position $P_d$ from the instant position P, and determine a set of electric currents i, wherein each electric current i of the set of electric currents i is applied to one of the plurality of coils 141 of the electromagnetic field generation system 104 such that the electromagnetic field generation system 104 applies the magnetic field magnitude $L_B$, the magnetic field angle $θ_B$ and the force vector $F_G$ to the ferrofluid droplet 102.

The system 100 further includes a camera 142 in communication with the controller 106, wherein the camera 142 provides an image of the ferrofluid droplet 102 to the controller 106 and wherein the controller 106 is operable to determine the instant position P, the instant stretch angle θ, and the instant stretch length L of the ferrofluid droplet 102 using the image provided by the camera 142 by an image processing module 166. In another aspect, one or more of the plurality of electromagnetic coils 141 are arranged horizontally along a horizontal plane and wherein one or more of the plurality of electromagnetic coils 141 are arranged at a predetermined angle relative to the horizontal plane.

In some embodiments, the controller 106 includes a position controller 163 operable to determine the force vector $F_G$ of the ferrofluid droplet 102, wherein the force vector $F_G$ manipulates the position P of the ferrofluid droplet 102 in an XY plane. The position controller 163 includes a first position controller 163A operable to determine the force vector $F_G$ necessary to manipulate the ferrofluid droplet 102 into the target position $P_d$ from the instant position P relative to the X axis, wherein the first position controller 163A is a proportional-integral-derivative controller, and a second position controller 163B operable to determine the force vector $F_G$ necessary to manipulate the ferrofluid droplet 102 into the target position $P_d$ from the instant position P relative to the Y axis, wherein the second position controller 163B is a proportional-integral-derivative controller. The controller 106 further includes a stretch length controller 161 operable to determine the magnetic field magnitude $L_B$ necessary to manipulate the ferrofluid droplet 102 into the target stretch length $L_d$ from the instant stretch length L, wherein the stretch length controller is a proportional-integral-derivative controller. The controller 106 further includes a stretch angle controller 162 operable to determine the magnetic field angle $θ_B$ necessary to manipulate the ferrofluid droplet 102 into the target stretch angle $θ_d$ from the instant stretch angle θ, wherein the stretch angle controller 162 is a proportional-integral-derivative controller.

The present disclosure further includes a method for control of a ferrofluidic droplet 102, the method comprising determining, by processor 302, an instant position P, an instant stretch angle θ and an instant stretch length L of a ferrofluid droplet 102; identifying, by processor 302, a position difference $E_p$ between instant position P and a target position $P_d$, a stretch angle difference ee between instant stretch angle θ and a target stretch angle $θ_d$, and a stretch length difference $e_L$ between instant stretch length L and a target stretch length $L_d$; determining, by processor 302, a magnetic field magnitude $L_B$ necessary to manipulate the ferrofluid droplet 102 into the target stretch length $L_d$ from the instant stretch length L, a magnetic field angle $θ_B$ necessary to manipulate the ferrofluid droplet 102 into the target stretch angle $θ_d$ from the instant stretch angle θ, and a force vector $F_G$ necessary to manipulate the ferrofluid droplet 102 into the target position $P_d$ from the instant position P; and determining, by the processor 302, a set of electric currents i, wherein each electric current i of the set of electric currents i is applied to one of a plurality of coils 141 of an electromagnetic field generation system 104 such that the electromagnetic field generation system 104 applies the magnetic field magnitude $L_B$, the magnetic field angle $θ_B$ and the force vector $F_G$ to the ferrofluid droplet 102. In some aspects, wherein a controller 106 is operable to determine the instant position P, the instant stretch angle θ, and the instant stretch length L of the ferrofluid droplet 102 using an image provided by a camera 142. In some aspects, the controller 106 is operable to determine the force vector $F_G$ by a position controller 163 using the position difference $E_p$ between instant position P and a target position $P_d$, wherein the force vector $F_G$ manipulates the position P of the ferrofluid droplet 102 in an XY plane. The controller 106 is further operable to determine the magnetic field angle $θ_B$ by a stretch angle controller 162 using stretch angle difference ee between instant stretch angle θ and a target stretch angle $θ_d$, wherein the magnetic field angle $θ_B$ manipulates the stretch angle θ of the ferrofluid droplet 102. The controller 106 is operable to determine the magnetic field magnitude $L_B$ by a stretch length controller 161 using stretch length difference ei between instant stretch length L and a target stretch length $L_d$, wherein the magnetic field magnitude $L_B$ manipulates the stretch length L of the ferrofluid droplet 102. The method is iteratively repeated until the instant position P, the instant stretch angle θ, and the instant stretch length L of a ferrofluid droplet 102 are at the target position $P_d$, the target stretch angle $θ_d$, and the target stretch length $L_d$.

DETAILED DESCRIPTION

The present disclosure discusses a system and associated method for control of a ferrofluid droplet. More specifically, various embodiments of systems and methods are disclosed herein for employing a drop of magnetically actuated ferrofluid to perform amoeba-inspired functions including splitting, regeneration, squeezing through narrow passages, particle engulfment and pushing, and flow induction. In some embodiments, a shape, position and length of the ferrofluid droplet is controlled using an electromagnetic field generation system. Position and shape control, as well as simultaneous position and shape control, is achieved by generation and manipulation of controlled magnetic fields surrounding the ferrofluid droplet. A dynamic controller implemented by the system is further described herein for precisely manipulating position and shape of the ferrofluid droplet using the electromagnetic field generation system. Verification and validation of the controller is shown through photographs of the ferrofluid droplet achieving various maneuvers and functionalities including splitting and recombination, engulfing particles, manipulating particles, generating flow through a microfluidic channel, following paths, and squeezing through channels is further provided. Referring to the figures, various embodiments of a system for control of a ferrofluid droplet are illustrated and generally indicated as 100 in FIGS. 1-11.

System Overview

Referring to FIGS. 1, 2 and 3, a system 100 for controlling position and shape of a ferrofluid droplet 102 is shown. Referring to FIG. 1A, the system 100 includes an electromagnetic field generation system 104 having a plurality of coils 141 angled towards the ferrofluid droplet 102, the electromagnetic field generation system 104 being operable to modulate a current i for each coil 141 which in turn modulates a magnetic field B collectively emanating from each coil 141 of the electromagnetic field generation system 104. Due to inherent magnetic properties of ferrofluid, a shape (defined by stretch length L and stretch angle θ) and position (P) of the ferrofluid droplet 102 are directly affected by the magnetic field B emanating from each coil 141 of the electromagnetic field generation system 104. The system 100 incorporates a feedback-based controller 106 for observing position P and shape (L, θ) of the ferrofluid droplet 102 and modulating the current i for each of the plurality of coils 141 to achieve a desired shape (L, θ) and position P of the ferrofluid droplet 102.

Figure 9:
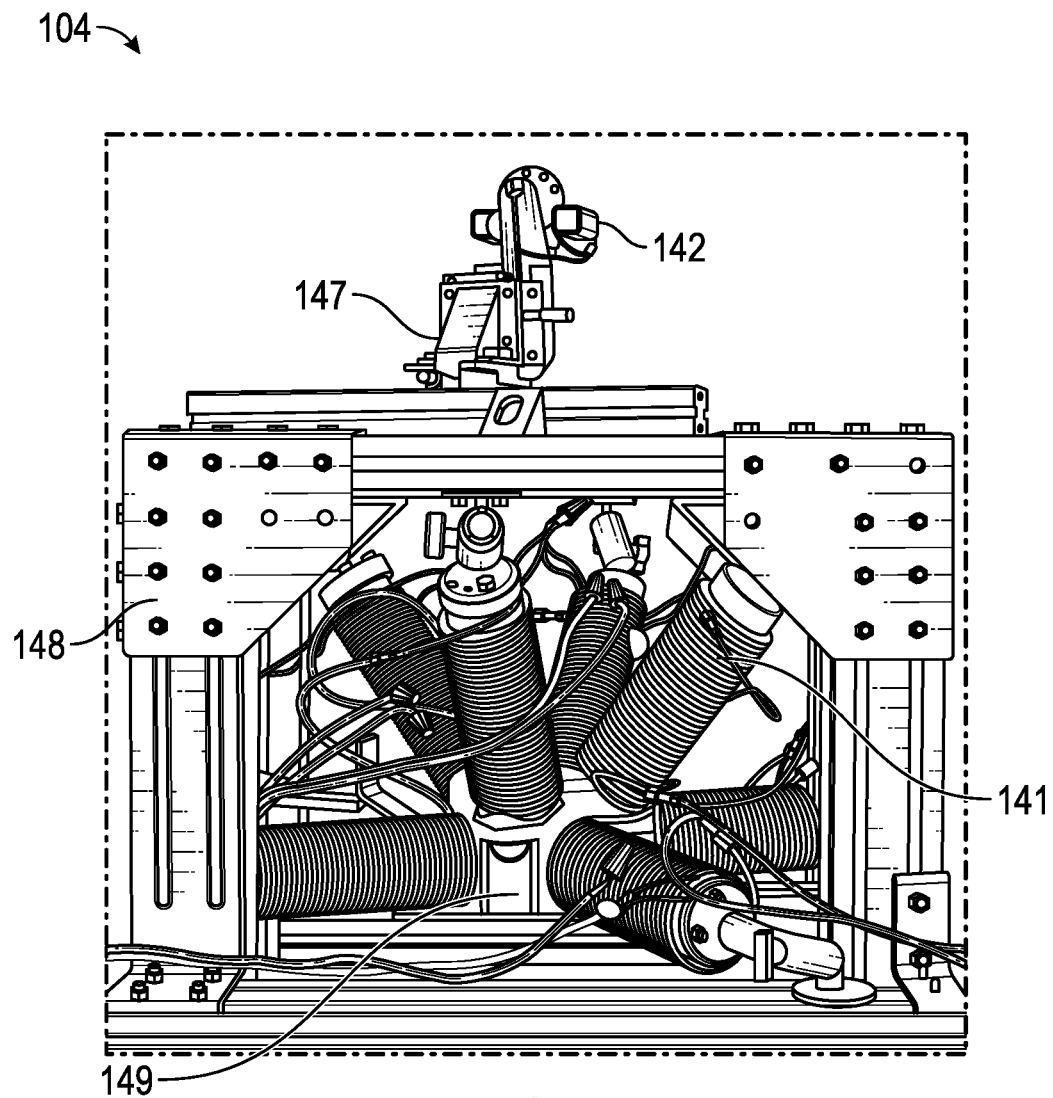
FIG. 9 is a photograph showing the electromagnetic field generation system.

Referring directly to FIG. 1A, a target stretch length $L_d$, a target stretch angle $\theta_d$, and a target position $P_d$ of the ferrofluid droplet 102 are selected and accepted as input to the controller 106. In some embodiments, the controller 106 may be embodied as processor 302 (FIG. 9). The controller 106 also receives an observed instant stretch length L, instant stretch angle $\theta$, and instant position P currently held by the ferrofluid droplet 102 and determines respective differences between target parameters ($L_d$, $\theta_d$, $P_d$) and instant parameters (L, $\theta$, P) (i.e. how the ferrofluid droplet 102 needs to change its shape/position to meet the target parameters). These differences are noted as $e_L$ for stretch length difference, $e_\theta$ for stretch angle difference and Ep for position difference. These differences ($e_L$, $e_\theta$, $E_P$) are taken as input into respective sub-controllers, namely a stretch length controller 161, a stretch angle controller 162, and a position controller 163. Each of these sub-controllers 161, 162 and 163 are responsible for determining a set of magnetic field parameters which would need to be applied by the electromagnetic field generation system 104 in order to manipulate the ferrofluid droplet 102 into the target shape and position. The outputs of each sub-controller 161, 162 and 163 are used to determine an optimal current i for each coil to generate the magnetic field B required to manipulate the ferrofluid droplet 102 into the target shape $L_d$, $\theta_d$ and position $P_d$. This process is iteratively repeated until the task is finished.

As further shown in FIGS. 1A, 1B and 1C, to generate the instant stretch length L, stretch angle $\theta$ and position P=($P_X$; $P_Y$), a camera 142 is situated above the ferrofluid droplet 102 to capture an image of the ferrofluid droplet 102. The image is processed by image processing module 166 to extract an instant position P, stretch length L and stretch angle $\theta$ of the ferrofluid robot 102. The instant position P, stretch length M and stretch angle $\theta$ as extracted by the image processing module 166 are defined in FIGS. 1B and 1C. This instant stretch length L, instant stretch angle $\theta$ and instant position P are then used to determine the differences $e_L$, $e_\theta$ and $E_P$ as described above.

The stretch length controller 161, stretch angle controller 162 and position controller 163 are proportional-integral-derivative (PID) controllers which accept the stretch length difference $e_L$, stretch angle difference $e_\theta$ and position difference $E_P$. The stretch length controller 161 uses the stretch length difference $e_L$ to determine a magnitude $L_B$ of the magnetic field B needed to manipulate the ferrofluid droplet 102 from the instant stretch length L to the target stretch length $L_d$. Similarly, the stretch angle controller 162 uses the stretch angle difference $\theta_L$ to determine an angle $\theta_B$ of the magnetic field B which is required to manipulate the ferrofluid droplet 102 from the instant stretch angle $\theta$ to the target stretch angle $\theta_d$. The position controller 163 can be comprised of two identical PID controllers (one for movement in the X axis and one for movement in the Y axis) and uses the position difference $E_P$ to determine a force vector $F_G$ in the XY planes that the magnetic field B would need to apply to the ferrofluid droplet 102 in order to move the ferrofluid droplet 102 from the instant position P to the target position $P_d$.

Outputs from the stretch length controller 161, stretch angle controller 162 and position controller 163 are used as input to a current determination module 164 which determines a set of optimal electric currents i to be applied to each individual coil 141 of the electromagnetic field generation system 104 which will induce the magnetic field magnitude $L_B$, magnetic field angle $\theta$ a, and force vector $F_G$ necessary to manipulate the ferrofluid droplet 102 into the target position.

FIG. 2 illustrates a method 200 for execution by the feedback controller 106 of the system 100. Referring to block 202 of FIG. 2, instant parameters (L, $\theta$, P) of the ferrofluid droplet 102 are obtained from the image processing module 166, including stretch length L, stretch angle $\theta$ and instant position P. The instant parameters are compared with target parameters $L_d$, $\theta_d$ and $P_d$ to produce respective differences between each property, expressed as:

$$E_L = L_d - L$$

$$e_\theta = \theta_d - \theta$$

$$E_P = P_d - P$$

At block 204, the respective differences $e_L$, $e_\theta$ and $E_P$ are fed into respective controllers 161, 162 and 163 for determining the necessary magnetic field magnitude $L_B$, magnetic field angle $\theta_B$ and force $F_G$ to be applied in both the X and Y planes. Referring to block 206, the magnetic field magnitude $L_B$, magnetic field angle $\theta_B$ and force $F_G$ are used to identify a set of electrical current values I using the current determination module 164. The set of electrical current values i, when each applied to each individual coil 141 of the electromagnetic field generation system 100, have a linear relationship with the magnetic field B emanating from each coil 141. Due to the inherent magnetization properties of the ferrofluid droplet 102, the magnetization of the ferrofluid droplet 102 is directly affected by the external magnetic field B acting on the ferrofluid droplet 102. Thus, the act of modulating each of the electrical current values i applied individually to each coil 141 of the electromagnetic field generation system 100 directly influences position P, stretch length L and stretch angle $\theta$ of the ferrofluid droplet 102 through application of the external magnetic field B.

At block 208, feedback is generated by observing position P, stretch length L and stretch angle $\theta$ of the ferrofluid droplet 102 using the camera 142 situated above the ferrofluid droplet 102. Images from the camera 142 are processed using the image processing module 166 to extract position P, stretch length L and stretch angle $\theta$ as shown in FIGS. 1B and 1C. This output is used as input to at block 202, where the method 200 is iteratively repeated until the ferrofluid droplet 102 has completed its task.

Control of the Droplet's Position and Shape

One approach for controlling the position and shape of the ferrofluid droplet 102 is to utilize a dynamic model of the ferrofluid droplet 102 interacting with the environment as well as the magnetic fields and design a model-based controller 106 for it. This model would be required to capture complex dynamics usually described by a set of partial differential equations, which in most cases may not be solved analytically. Even for the cases that the analytical solution could be obtained, it is still required to solve the inverse problem to find the required currents i of the coils 141 for every desired position $P_d$ and shape ($L_d$, $\theta_d$) of the ferrofluid droplet 102. Furthermore, physical terms found in such a model need to be observed or estimated for each control loop iteration. Here, visual feedback is used to get the real-time information of the ferrofluid droplet 102. By processing the feedback images obtained from the camera 142, information about the position and shape of the ferrofluid droplet 102 is computed and provided to the controller 106.

The first step in defining the control problem is to standardize the shape definition of the ferrofluid droplet 102. If abrupt changes are not applied to the resultant magnetic field B, to a very good approximation, the ferrofluid droplet 102 can be modelled as an ellipsoid. The projection of this ellipsoid onto a plane crossing its center parallel to the horizon is an ellipse in 2D, which can be easily seen from the camera 142 installed above the workspace. This ellipse and its corresponding parameters are used to characterize the position and shape of the ferrofluid droplet 102. It is worthy to note that the shape of the ferrofluid droplet 102 in 2D is determined according to FIG. 1B using two parameters: the length of the ellipse major axis radius, L (stretch length), and its orientation, e (stretch angle). The position of the ferrofluid droplet 102 is defined as that of the ellipse center point specified using two variables, $P_x$ and $P_y$. Thus, assuming the ferrofluid droplet 102 has constant volume and that no intense and instantaneous magnetic field changes are applied, four variables are needed to completely describe the shape and position of the ferrofluid droplet 102. The electromagnetic field generation system 104 can be used for controlling the above mentioned four variables through a multi-input-multi-output (MIMO) controller.

Referring to FIG. 1A, the controller 106 comprises 3 PID sub-controllers: a position controller 163 including two identical PID controllers 163A and 163B for manipulating magnetic field gradient $F_G$ to control the position P of the ferrofluid droplet 102 in the XY plane, a stretch angle controller 162 on the magnetic field direction $\theta_B$ to control the stretch direction $\theta$ of the ferrofluid droplet 102, and lastly, a stretch length controller 161 on the magnitude $L_B$ of the magnetic field B to control the stretch length ferrofluid droplet 102. These sub-controllers 161, 162, 163 are all closed loop, relying on visual feedback from the camera 142 to maintain control. The feedback loop uses the captured images of the workspace to compute four instant parameters: $P_x$, $P_y$, L, and $\theta$ as shown in FIGS. 1B and 1C. Finally, the outputs of these three blocks are processed through an equation relating the currents i within the coils 141 to the desired magnetic field and gradient at the position of the ferrofluid droplet 102. This relationship is solved to obtain the required current values for either 4 or 8 coil control, composing the final controller command sent to the coils 141.

To control the position of the ferrofluid droplet 102, the position error vector, $E_P$, of the desired location, $P_d$, with respect to the current position of the ferrofluid droplet 102, $P=(P_x, P_y)$, is calculated as $E_P=P_d-P$. The resultant force acting on the ferrofluid droplet 102 should be toward the desired location; that is, the direction of $E_P$. The forces applied on the ferrofluid droplet 102 in the x and y directions are defined by the $F_{desired}$ terms in Equation 3 (below). In fact, these are the variables that the position PID sub-controllers 161, 162, 163 are programmed to manipulate to achieve the desired location.

The electromagnetic field generation system 104 is designed with the intention that the magnetic field H generated by each coil 141 is in the linear regime over the entire workspace. Due to the relative sizes of the electromagnetic coils 141 and the workspace 149, the magnetic field lines for each coil 141 are nearly parallel to its axis. However, a thorough calibration process executed by a calibration module 165 in which the field and gradient contributions of each coil 141 at different current values are tabulated is necessary to accurately calculate the required currents i. The force needed to act on the ferrofluid droplet 102 to move it towards the desired position $P_d$ from the instant position P as determined using the position difference $E_P$ can be written as:

$$F = \begin{bmatrix} F_x \\ F_y \end{bmatrix} = K_{PP}E_P + K_{DP}\dot{E}_P + K_{IP}\int E_P dt \tag{1}$$

where $K_{PP}$, $K_{PP}$, and $K_{IP}$ are three positive constants representing the proportional, derivative, and integral gains of the controller 163, tuned manually.

FIG. 1A shows control architecture of the ferrofluid droplet 102. $L_d$, $\theta_d$, and $P_d$ are the desired stretch length, stretch angle, and position. Errors for each parameter $e_L$, $e_\theta$, and $E_P$, act as inputs to their respective sub-controllers 161, 162 and 163. The controller outputs, $L_B$, $\theta_B$, and $F_G$ are the stretch length, stretch angle, and forces that need to be applied to the ferrofluid droplet 102 so it can transition to the desired location $P_d$ and shape $L_d$, $\theta_d$. These outputs are input to Equation 3, which relates these output parameters to current i in the coils 141. Feedback parameters are collected via computer vision. FIG. 1B illustrates defines position control parameters as the vector error between current robot position P and desired position $P_d$ in a frame of reference xy rotated 45° from the image frame of reference $x_0y_0$. Similarly, FIG. 1C defines shape control parameters B and L as the stretch angle and stretch length of the ferrofluid droplet 102.

While the ferrofluid droplet 102 does not move under zero resultant force, it can be stretched proportional to and in the direction of, the magnetic field vector. In particular, magnitude, $L_B$, and angle, $\theta_B$, of the magnetic field vector determine the magnetization of the individual internal particles within the ferrofluid droplet 102, and thus the intensity to which the ferrofluid droplet 102 is caused to align with the magnetic field H. Therefore, to control the shape of the ferrofluid droplet 102, the angle $\theta_B$ and magnitude $L_B$ of the magnetic field H is defined in terms of the errors in stretch angle, $e_\theta$, and stretch length $e_L$.

$$\theta_B = K_{P\theta}e_\theta + K_{D\theta}\dot{e}_\theta + K_{I\theta}\int e_\theta dt$$

$$L_B = K_{PL}e_L + K_{DL}\dot{e}_L + K_{IL}\int e_L dt \tag{2}$$

where $K_{P\theta}$, $K_{I\theta}$, $K_{D\theta}$, $K_{PM}$, $K_{DM}$, and $K_{IM}$ are positive constants representing the proportional, derivative, and integral gains of the sub-controllers 161 and 162, tuned manually. In some embodiments, the gains of the sub-controllers 161, 162 and 163 are as follows: for the position controllers 163, $K_{PP}=0.5$, $K_{IP}=0.002$, $K_{DP}=0.1$; for the stretch length controller 161 the droplet, $K_{PM}=0.08$, $K_{IM}=0.02$, $K_{DM}=0.02$; and lastly, for the stretch angle controller 162 of the droplet, $K_{P\theta}=0.5$, $K_{I\theta}=0.05$, $K_{D\theta}=0.5$. As with all controllers, the response of the system can be tuned to fit a desired behavior by altering these gains. The gains presented in this study were tuned specifically for the experiments. It is known that ferrofluid gets stretched along its magnetization vector which is always aligned with the external magnetic field. By applying control on the magnetic field direction $\theta_B$, the stretch angle $\theta$ and length L can be controlled.

Magnetic field direction $\theta_B$ can be used to define the desired stretch angle $\theta$. The magnetization of ferrofluid is proportional to the external magnetic field acting on ferrofluid. The applied magnetic gradient $F_G$ and the magnetization of the ferrofluid determine the force applied on the ferrofluid.

The electrical current i in each coil 142 to generate the required magnetic field B and gradient $F_G$ can be determined considering the linear relation of magnetic field B and electrical current i. In some embodiments, this step is performed by the current determination module 164 of FIG. 1A. Net magnetic flux density and gradient can be calculated using the linear superposition of each electromagnetic coil's 141 magnetic flux density and gradient contribution. As alluded to earlier, the contribution of each coil is measured through a calibration process for 1 A current. The required current ($i_0 \ldots i_7$) to achieve the desired forces $F_{desired}$ and magnetic field $B_{desired}$ can be calculated as:

$$\begin{bmatrix} i_0 \\ \vdots \\ i_7 \end{bmatrix} = \begin{bmatrix} \beta(P) \\ (M(\beta(P)))^T \beta_x(P) \\ (M(\beta(P)))^T \beta_y(P) \\ (M(\beta(P)))^T \beta_z(P) \end{bmatrix}^\dagger \begin{bmatrix} B_{desired} \\ F_{desired} \end{bmatrix} \quad (3)$$

$$\begin{bmatrix} i_0 \\ \vdots \\ i_7 \end{bmatrix} = A_{B,F}(M, P)^\dagger \begin{bmatrix} B_{desired} \\ F_{desired} \end{bmatrix} \quad (4)$$

where β(P) represents the magnetic field contribution of each of the plurality of electromagnetic coils 141 at a particular position P. Currents ($i_0 \ldots i_7$) are representative of currents for each coil 141 when 8 coils 141 are used, however in the embodiment of four coils 141, currents ($i_0 \ldots i_3$) are considered. $\beta_x(P)$, $\beta_y(P)$, $\beta_z(P)$ are the gradients of the calibration matrix in each direction at the position P, $B_{desired}$ is the flux density in each direction, $F_{desired}$ is the desired force in each direction, M is the magnetization vector of the ferrofluid droplet 102 under influence of a particular magnetic field, and † represents the pseudo-inverse. For this application, the magnetization vector M is assumed to be a unit vector in the direction of $B_{desired}$.

The ferrofluid droplet 102 is assumed to be a magnetized body described by a magnetic moment M. As such, the magnetic moment is dependent on the applied field and can rotate with respect to the body and its magnitude can vary greatly with changes in the applied field. The torque on the magnet is expressed as such:

$$T = M \times B \quad (5)$$

where B is the applied magnetic field's flux density at the location of M. The torque tends to align the magnetic moment with the applied field. The magnetic force is expressed as:

$$F = (M \cdot \nabla) B \quad (6)$$

Since there is no electric current flowing through the region occupied by the body, Maxwell's equations provide the constraint $\nabla \times B = 0$. This allows Eq. (6) to be expressed in this form:

$$F = \begin{bmatrix} \frac{\partial B}{\partial x} & \frac{\partial B}{\partial y} & \frac{\partial B}{\partial z} \end{bmatrix}^T M \quad (7)$$

With the static arrangement of electromagnets, each electromagnet creates a magnetic field throughout the workspace that can be pre-calculated. At any point P in the workspace, the magnetic field due to actuating a given electromagnet can be expressed by the vector $B_e(P)$, whose magnitude varies linearly with the current through the electromagnet and as such can be described as a unit-current vector multiplied by a scalar current value:

$$B_e(P) = \tilde{B}_e(P) i_e \quad (8)$$

Due to the design of the present system 100, it can be assumed that the magnetic field B at a point in the workspace is the sum of the contribution of the individual electromagnetic coils 141. This linear summation of fields can be expressed as follows $$B(P) = \begin{bmatrix} \tilde{B}_1(P) & \ldots & \tilde{B}_n(P) \end{bmatrix} \begin{bmatrix} i_1 \\ \vdots \\ i_n \end{bmatrix} = \beta(P) I \quad (9)$$

Considering (5), (7), and (9), the magnetic torque and forces on the ferrofluid can be expressed as follows:

$$\begin{bmatrix} T \\ F \end{bmatrix} = \begin{bmatrix} Sk(M)\beta(P) \\ M^T \beta_x(P) \\ M^T \beta_y(P) \\ M^T \beta_z(P) \end{bmatrix} \begin{bmatrix} i_1 \\ \vdots \\ i_n \end{bmatrix} = A_{T,F}(M, P) I \quad (10)$$

That is, for each ferrofluid pose, the n electromagnet currents are mapped to a torque and force through a 6×n actuation matrix $A_{T,F}(M, P)$. For a desired torque/force vector, the choice of currents closest to the desired torque/force value can be found using the pseudo-inverse (†).

$$I = A_{T,F}(M, P)^\dagger \begin{bmatrix} T_{desired} \\ F_{desired} \end{bmatrix} \quad (11)$$

Because the ferrofluid droplet 102 can align with the applied field unimpeded, rather than explicitly controlling the torque one can control the field to the desired orientation and then explicitly control the force of the ferrofluid droplet 102.

$$\begin{bmatrix} B \\ F \end{bmatrix} = \begin{bmatrix} \beta(P) \\ M^T \beta_x(P) \\ M^T \beta_y(P) \\ M^T \beta_z(P) \end{bmatrix} \begin{bmatrix} i_1 \\ \vdots \\ i_n \end{bmatrix} = A_{B,F}(M, P) I \quad (12)$$

The current I is then set as follows $$I = A_{B,F}(M, P)^\dagger \begin{bmatrix} B_{desired} \\ F_{desired} \end{bmatrix} \quad (13)$$

In this case, the ferrofluid droplet 102 will align with the applied field under open-loop control. If the direction of B does not change quickly, it is reasonable to assume that M is always aligned with B, which means that one must estimate the magnitude of M and measure the position P of the ferrofluid droplet 102.

The relation between the magnitude of magnetization and external magnetic field strength can be expressed using the Langevin law:

$$M(H) = M_s \left[ \coth(\gamma H) - \frac{1}{\gamma H} \right] \quad (14)$$

where $M_s$ is the saturation magnetization and $$\gamma = 3\frac{\chi_0}{M_s}$$

with $\chi_0$ being the initial value of magnetic susceptibility.

Assuming that the ferrofluid droplet 102 takes the form of an ellipse with the major radius of a and a minor radius of b, the volume of a stretched droplet is:

$$V = \frac{4}{3}\pi ab^2 \quad (15)$$

Considering a constant volume for the ferrofluid droplet 102, the major and minor radii are inversely proportional $$\left(a \propto \frac{1}{b^2}\right).$$

Besides, me curvature or the ferrofluid droplet 102 at the vertex point is:

$$C = \frac{a}{b^2} \propto a^2 \quad (16)$$

Thus, increased curvature leads to an increase in the major radius, a. Assuming incompressibility, this change results in a decreased minor radius, b.

Shape Control Results

Figure 4A:
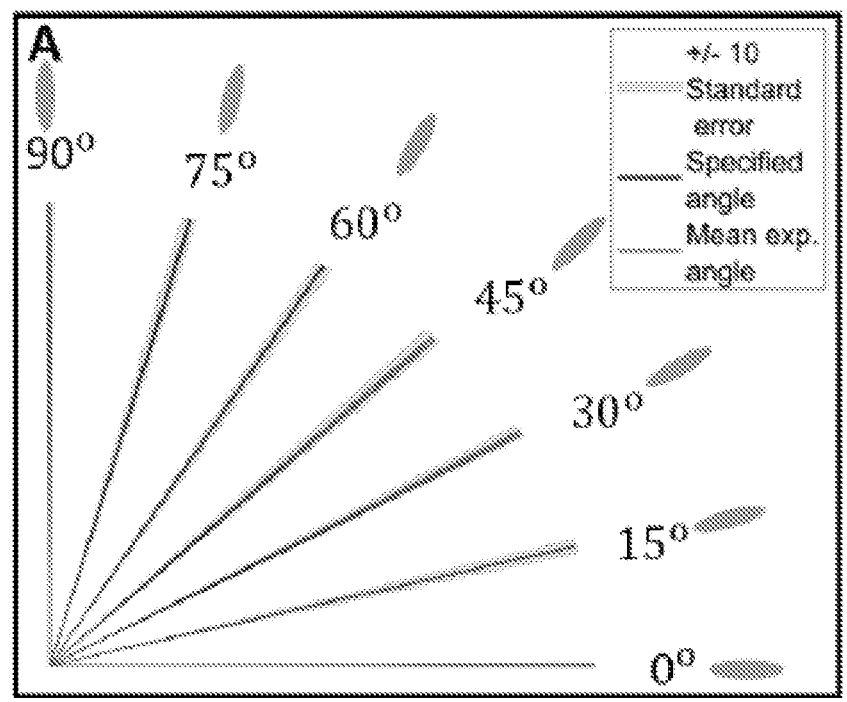
FIGS. 4A-4D is a series of graphical representations showing shape control for the ferrofluid droplet of FIG. 1A, including stretch angle for a 4-coil electromagnetic field generation system (FIG. 4A), stretch angle for an 8-coil electromagnetic field generation system (FIG. 4B), stretch length for the 4-coil electromagnetic field generation system (FIG. 4C), and stretch length for the 8-coil electromagnetic field generation system (FIG. 4D)
Figure 4B:
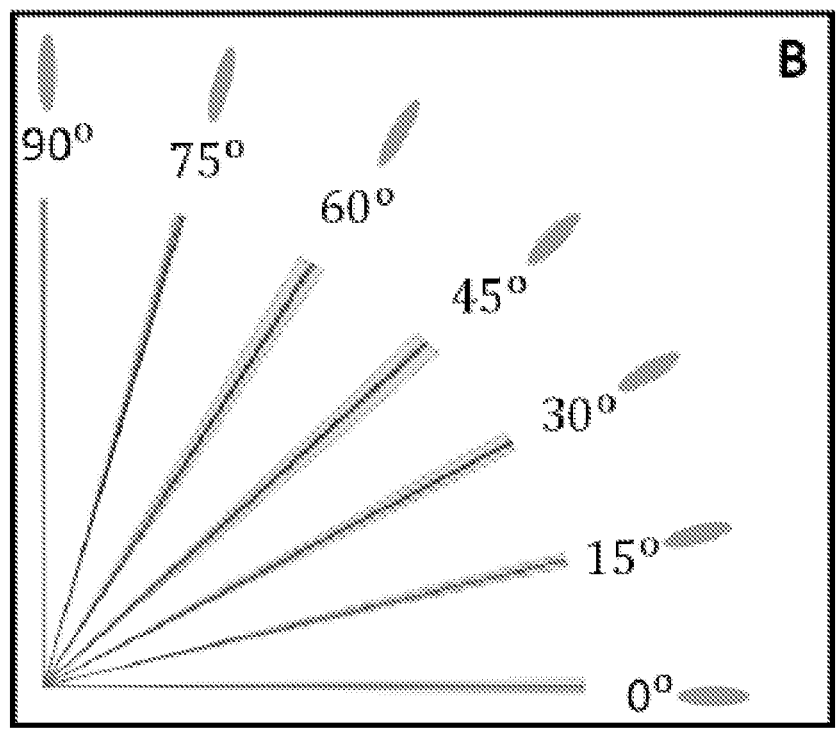
Figure 4C:
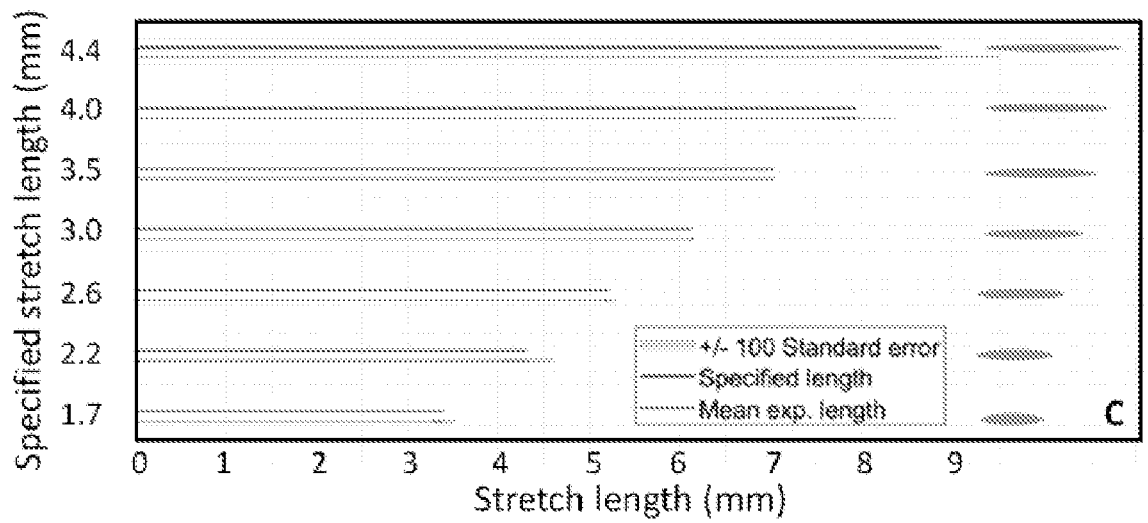
Figure 4D:
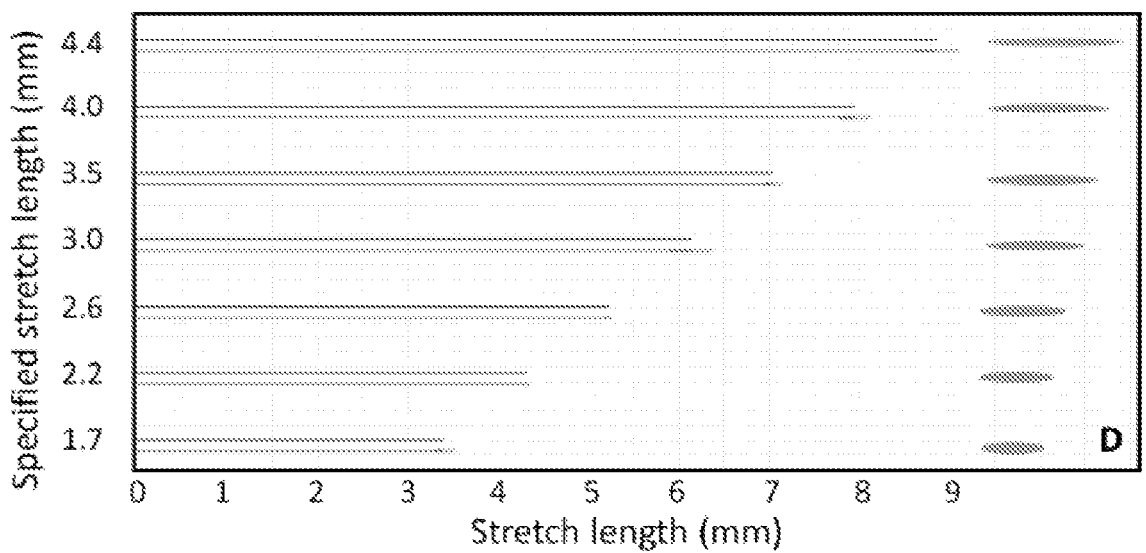

A key feature of the present system 100 is the ability to control the shape of the ferrofluid droplet 102, defined by two parameters shown in FIG. 1B: the major axis radius of an ellipse imposed on the silhouette of the ferrofluid droplet 102, M (stretch length, mm); and the angle between that ellipse's major axis and the horizontal axis, θ (stretch angle, degrees). Shape control experiments demonstrate performance of the stretch length and stretch angle control of the ferrofluid droplet 102, as presented in FIGS. 4A-4C. FIG. 4A plots the steady state performance of stretch angle control, showing mean experimental angle+/−1 standard error and the specified angle in the case of utilizing 4 coils 141 of the electromagnetic field generation system 104. FIG. 4B plots the same for the case of control using 8 coils 141 of the electromagnetic field generation system 104. The results are notably similar. Average and maximum error over all steady state angle measurements during this experiment is 0.7° and 5.8°, respectively, in the case of 4 coil control; and 0.1° and 5.9°, respectively, in the case of 8 coil control. Images of the ferrofluid droplet 102 are included in the figure to visualize stretch angle control. Stretch length control capabilities are plotted in FIGS. 4C and 4D for seven different specified stretch length radii ranging from 1.7 mm to 4.4 mm. Experimental steady state mean stretch length+/−1 standard error is plotted under the specified stretch length. Mean stretch length is calculated by taking the average of the stretch length over 100 frames during the experiment after the angle has settled. Average and maximum error over all steady state mean stretch length measurements is less than 0.1 mm which is the minimum resolution that can be measured with this setup, for both 4 and 8 coil control methods. Robot images as shown in FIGS. 4A-4D visualize relative stretch length, and are not to scale with respect to any axis. The ferrofluid droplet 102 shape can be controlled at any position in the workspace, and to any stretch intensity up to the ferrofluid droplet 102 droplet splitting.

Figure 5:
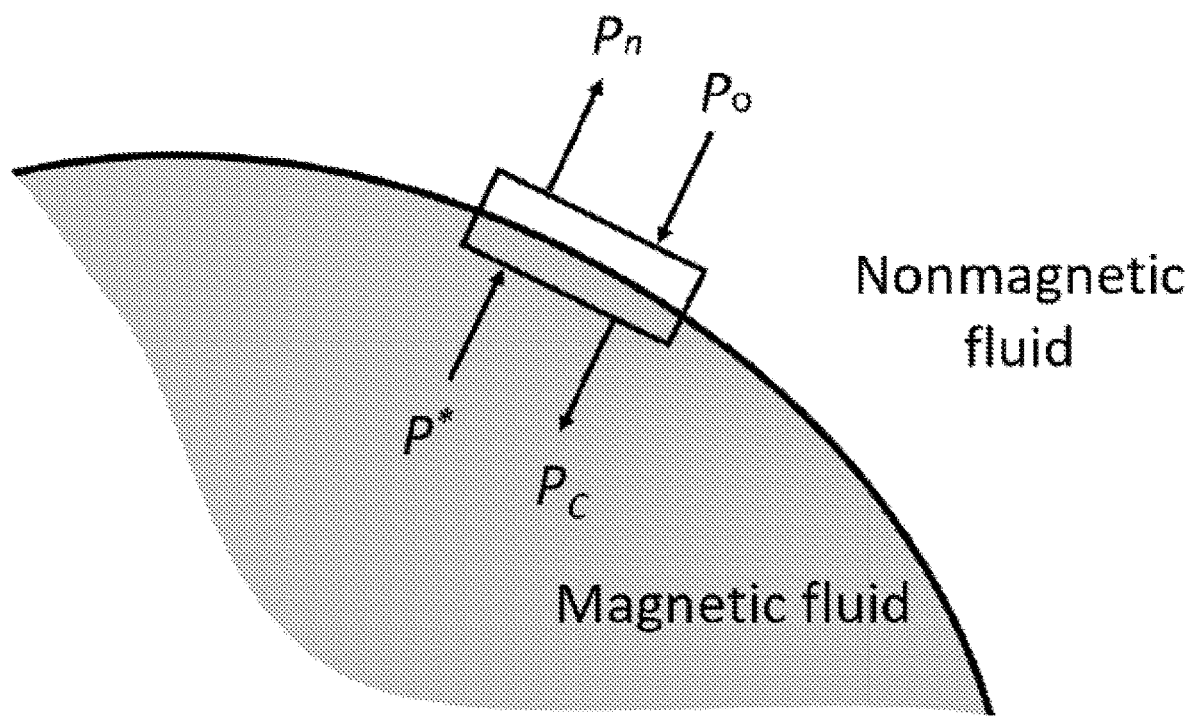
FIG. 5 is a diagram showing balances of normal stresses at a surface of the ferrofluid droplet of FIG. 1A and a surrounding fluid.

The shape of a ferrofluid droplet 102 is indeed enforced by the stresses acting on its boundary. Considering an inviscid, isothermal, and incompressible ferrofluid droplet surrounded by a nonmagnetic fluid, the balance of stresses at the boundary between the ferrofluid droplet 102 and the surrounding fluid can be expressed using Equation 17, and as shown in FIG. 5.

$$P^* + P_n = P_o + P_c \quad (17)$$

In this equation, composite pressure (P*) and fluid-magnetic pressure ($P_m$) are bulk pressures defined as $P^* = P(\rho, T) + P_m$ where $P(\rho, T)$ represents the thermodynamic pressure ($\rho$ and T are the density and temperature of the ferrofluid) and $P_m = \mu_0 \int_0^H M dH$ ($\mu_0$, H and M are the permeability of vacuum, the external magnetic field strength, and the corresponding magnetization of the ferrofluid, respectively). Furthermore, magnetic normal traction ($P_n$) and capillary pressure ($P_c$) are the interfacial force densities.

$$P_n = \mu_0 \frac{M_n^2}{2}$$

where $M_n$ is the normal component of the magnetization. $P_c = 2C\sigma$, where C is the curvature, and σ is the surface tension. Moreover, $P_o$ is the pressure applied by the nonmagnetic fluid on the droplet boundary.

Figure 6:
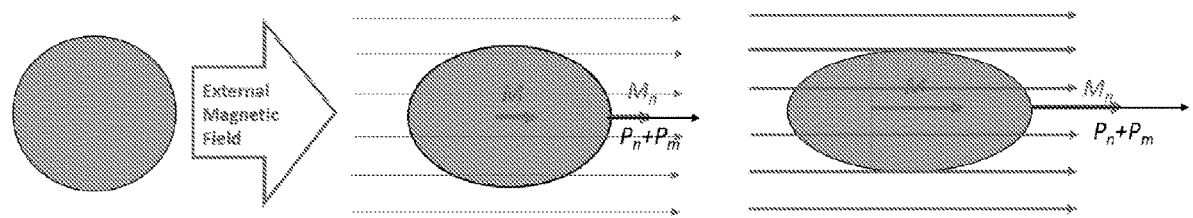
FIG. 6 is a diagram illustrating alignment of the ferrofluid droplet of FIG. 1A with the external magnetic field.

In Equation 17, the magnetic surface force density ($P_n + P_m$) indicates the contribution of the external magnetic field on the normal stresses at the interface of the ferrofluid droplet 102 and its surrounding fluid. According to Equation 14, the magnetization of the ferrofluid changes with the external magnetic field strength. This, in turn, alters both $P_n$ and $P_m$ and thus, impacts the pressures on the boundary. Besides, Equation 17 implies that with constant thermodynamic pressure and in a stationary surrounding fluid, the capillary pressure counterbalances the changes in magnetic surface force density. Since the surface tension of the ferrofluidic droplet 102 in small magnetic fields can be considered constant, the curvature of the boundary is the factor responsible for changing the capillary pressure. Thus, by increasing the magnetic field strength, the curvature of the droplet boundary will change to balance the interfacial stresses. As changes in the magnetic surface force density are more significant at the points where the magnetization vector is normal to the boundary (along the magnetic field), the curvatures at those points experience larger variations. Hence, according to Equation 16, the largest stretch occurs in the direction of the magnetic field (FIG. 6). In short, as the magnetic field strength increases, the ferrofluid droplet 102 stretches along the direction of the magnetic field to balance the increased magnetic surface force density.

Combined Shape and Position Control Results

Position, stretch angle, and stretch length of the ferrofluid droplet 102 can be independently controlled by the magnetic field gradient, direction, and magnitude, respectively. Three independent proportional-integral-derivative (PI D) controllers 161, 162, 163 are used to control the ferrofluid droplet 102 (Equations 1 and 2) and as a result, any combination of the position and shape can be achieved.

Figures 7A, 7B:
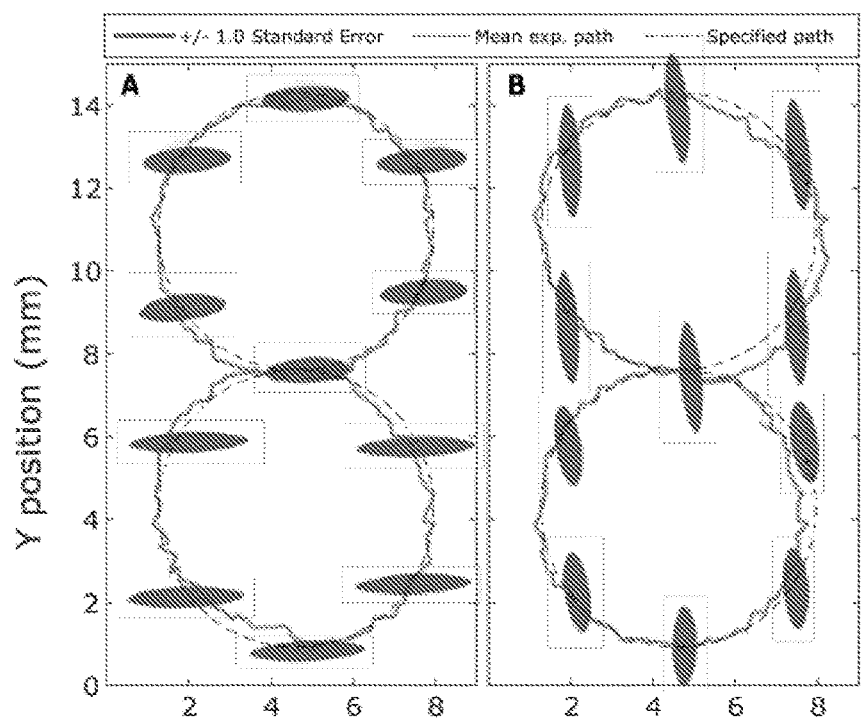
FIGS. 7A-7D is a series of graphical representations showing combined position and shape control of the ferrofluid droplet of FIG. 1A following a lemniscate path, including holding a horizontal stretch angle (FIGS. 7A and 7C) and holding a vertical stretch angle (FIGS. 7B and 7D) at different stretch lengths.
Figures 7C, 7D:
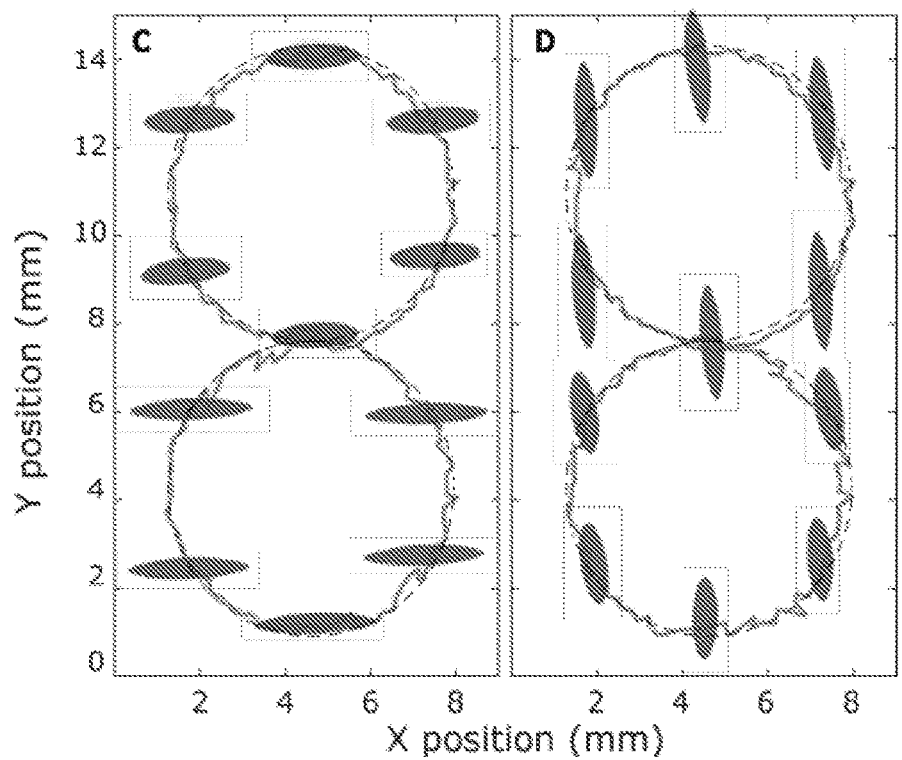

To demonstrate the ability to simultaneously control both position and shape, an experiment is performed in which the ferrofluid droplet 102 is tasked with following a specified path while holding specified stretch angles and lengths in four intervals. Results of this experiment are presented in FIGS. 7A-7D, where mean experimental path +/− one standard error and specified path are plotted together. The ferrofluid droplet 102 follows the lemniscate path twice over the course of one experimental trial, and as such the figure is split into two parts for clarity. FIGS. 7A and 7C display the mean experimental path +/− one standard error of the first half of the experiment, where the ferrofluid droplet 102 is set to a horizontal stretch angle and then to switch from one stretch length to a second stretch length after completing the first half of the lemniscate. Likewise, FIGS. 7B and 7C display part two of the experiment where the ferrofluid droplet 102 is set to hold a vertical path and switch from a first stretch length to a second stretch length after completing the first half of the lemnsicate path. For these experiments, the position, the stretch angle, and the stretch length is controlled in closed loop. Data for this figure is taken over five experimental trials. Images of the ferrofluid droplet 102 are underlaid beneath the plot to show the stretch angle and length changes over the course of the experiment. The average and maximum error of the experimental mean from the specified path for this experiment is 0.2 mm and 0.7 mm, respectively, for the 4 coil case; and 0.2 mm and 0.6 mm, respectively, for the 8 coil case.

FIGS. 7A-7D show combined position and shape control when following a lemniscate path. The lemniscate path is followed twice per experimental run: first holding a horizontal (FIGS. 7A and 7C) and then a vertical (FIGS. 7B and 7D) stretch angle at two stretch lengths. The specified path, experimental mean, and +/− one standard error are plotted with dashed blue line, solid pink line, and pink shade, respectively. Snapshots of the robot from corresponding time steps are overlaid on each plot. The size of these overlaid snapshots is reduced by half to improve visibility of the plots.

Although the eight coil control is singularity-free, the four coil control suffers from singularity when the stretch angle is 45 degrees (aligned with two coils). In this case, if the stretch angle needs to be maintained, the position control is feasible along the major axis of the ferrofluidic droplet 102 (i.e. along the axis of the two coils the droplet is aligned with).

As can be seen in FIGS. 5A-5D, there are consistent deviations from the path. It may be due to the momentum that the ferrofluidic droplet 102 picks up as it accelerates during certain parts of the path. As velocity is not controlled, the actual velocity of the droplet may result in the droplet overshooting the desired point, between controller iterations. Increasing the control frequency would mitigate this issue. However, control frequency and resolution of the image for visual feedback are competing parameters: in order to increase the control frequency the image resolution would need to be reduced, and vice versa. Coupled improvement of image resolution and control frequency could be achieved by improving the computational power of the system used to run the control program.

Functional Maneuvers Results

Utilizing the position and shape control capabilities quantified above, the ferrofluid droplet 102 is capable of performing complex motions and functional maneuvers, namely: subdivision, regeneration, particle engulfment, particle sorting, and flow induction. Each maneuver is defined in terms of the ferrofluid droplet 102 position P, stretch length L, and stretch angle θ, and is performed in closed loop control. Successful performance of such tasks are demonstrated and visualized in FIGS. 8A-8E. All of these experiments are performed using four coils 141.

Figure 8A:
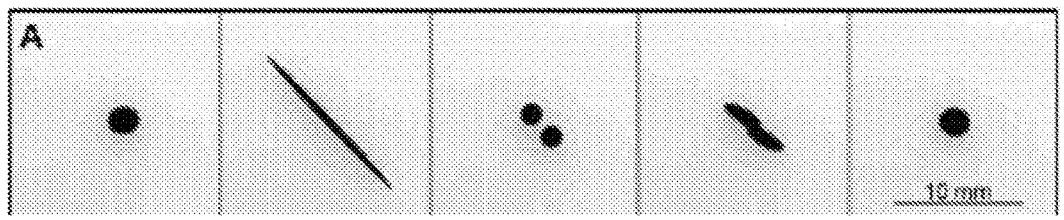
FIGS. 8A-8E are respective photographs showing functional maneuvers performed by the ferrofluid droplet of FIG. 1A, including closed loop separation and recombination of the ferrofluid droplet of FIG. 1A emulating mitosis and regeneration, respectively (FIG. 8A), closed loop pulsing to squeeze through a channel (FIG. 8B), particle engulfment utilizing closed loop position control to engulf and transport smaller particles (FIG. 8C), closed loop position and shape control to interact with and push particles to target locations (FIG. 8D), and closed-loop shape control to generate flow in a microfluidic channel (FIG. 8E)

FIG. 8A demonstrates the ability of the ferrofluid droplet 102 to split itself into separate parts and then recombine. The shape control scheme is applied to produce a short pulse at a specified stretch angle θ and at a very high stretch length L, such that the ferrofluid droplet 102 splits. Applying shape control at the same stretch angle but at a lower stretch length causes the smaller parts to contact one another, resulting in recombination via surface tension when allowed to return to rest.

Figure 8B:
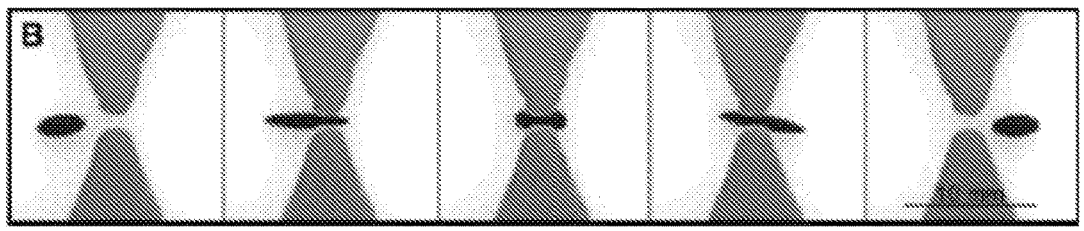

The ability of the ferrofluid droplet 102 to squeeze through a narrow channel is demonstrated in FIG. 8B. To accomplish this task, the closed-loop position control scheme is used to move the ferrofluid droplet 102 to the channel entrance, then a directed pulsing motion is induced by combining the position control scheme with automated pulsing shape control signals. This pulsing action allows the robot to make incremental progress as it squeezes itself through the channel. The channel opening is 1 mm at its narrowest point. The ferrofluid droplet 102 can also be moved through a narrow channel by increasing the stretch length without pulsing shape control; however, depending on the channel width, it may result in splitting due to a large aspect ratio and the resisting forces applied by the channel edges.

Figure 8C:

As is demonstrated in the image sequence in FIG. 8C, the ferrofluid droplet 102 can successfully "hunt" and engulf wettable colored particles. In the present disclosure, a "wettable" particle is defined as a particle which is able to be made adhesive or absorptive by the addition of a liquid, such as ferrofluid. When the ferrofluid droplet 102 used in this study is submerged in isopropyl alcohol, glass and polished acrylic are considered as non-wettable, while polyethylene and most other plastics are wettable materials. The colored particles used in this experiment are wettable polymer beads (Cospheric Innovations UVPMS-BR-1.20 Fluorescent Red Polyethylene Microspheres) placed in the workspace randomly. The positions of the particles are obtained optically at the beginning of the experiment. This demonstration utilizes a combination of the position control scheme described earlier and a colored particle detection and tracking subprogram. The ferrofluid droplet 102 follows a path in closed loop which sequentially passes through the colored particles in a chosen order. The ferrofluid droplet 102 carries the engulfed particles as it continues along its path to engulf subsequent particles. This effectively accomplishes clearing the workspace and transporting the particles to the end location of the ferrofluid droplet 102. It is, however, observed that the ferrofluid droplet 102 becomes less responsive to the actuating magnetic field after gathering multiple particles. This may be due to the ferrofluid droplet 102 carrying extra weight that does not contribute to its magnetic properties. It is important to note that this functional maneuver is achievable with particles that are wettable by the ferrofluid.

Figure 8D:
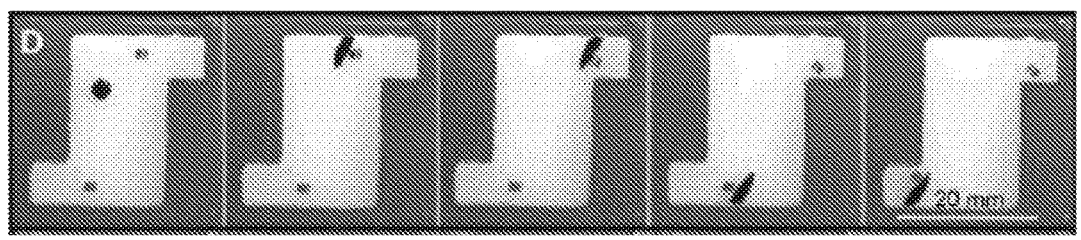

In FIG. 8D, the ferrofluid droplet 102 is shown completing a task in which it must push two colored particles into separate target areas. This demonstration utilizes position control to place the ferrofluid droplet 102 to the side of the particle in preparation to push, then uses a combination of shape and position control to push the particle into the target zone. The particles are colored glass cylinders of 1.3 mm diameter and 1.6 height. Glass is chosen as it is not wettable by the ferrofluid in 70% isopropyl alcohol. In addition, cylindrical particles are chosen for ease of pushing due to reduced friction through rolling. It is important to note that, in contrast to the engulfment maneuver, manipulation and sorting are achievable for particles that are not wettable by the ferrofluid.

Figure 8E:
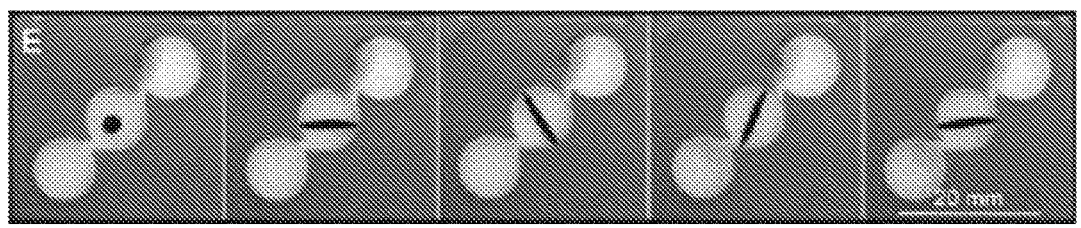
Figure 10:
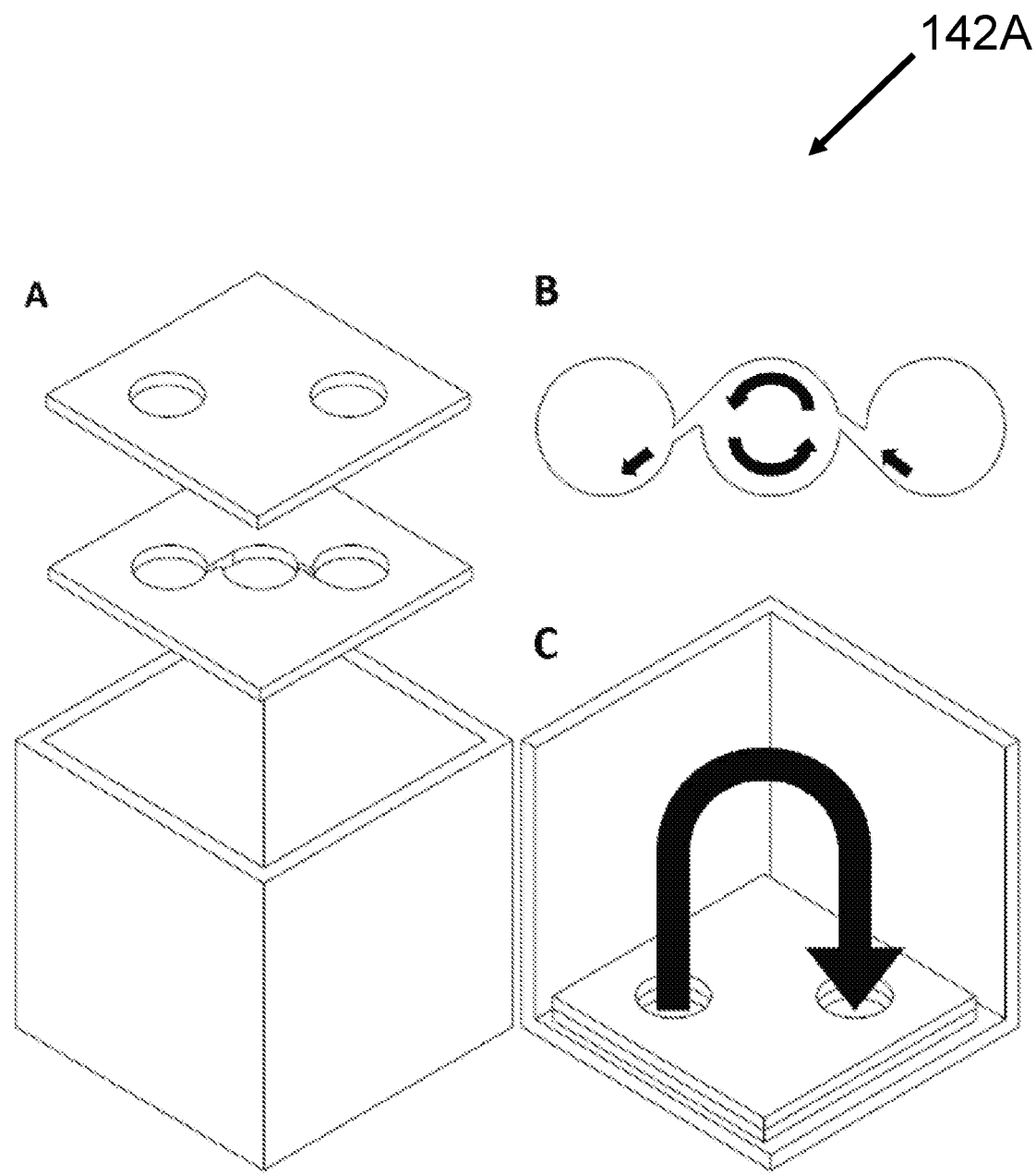
FIG. 10 is an illustration showing a pump assembly for testing the functional maneuvers shown in FIG. 8E.

As shown in FIG. 8E, flow can be induced in a microfluidic channel by controlling the shape of the ferrofluid droplet 102. This experiment utilizes close-loop shape control only, maintaining stretch length and manipulating stretch angle incrementally to produce a rotary pump like mechanism. The microfluidic pump in FIG. 8E, also shown in FIG. 10, is designed with three chambers; one to hold colored dye to visualize flow (top), one to contain the ferrofluid droplet 102 (mid), and the last containing the carrier fluid to qualify flow (bottom). Two channels connect the three cells and are designed as nozzles/diffusers oriented to bias flow in the desired direction. The channels are also oriented to take advantage of the rotation of the ferrofluid droplet 102. A schematic of the rotational pump design is presented in FIG. 10.

The Experimental Setup

An exemplary non-limiting embodiment of the electromagnetic field generation system 104 is shown in FIG. 9. The electromagnetic field generation system 104 produces and manipulates the actuating magnetic field B. Eight stationary current controlled electromagnetic coils 141 are used in the setup. In some embodiments, the electromagnetic field generation system 104 includes four coils 141 arranged in-plane horizontally, equiangular around the workspace 149 and facing inward; and the remaining four coils 141 staggered 45 degrees both around the workspace and up towards the top of the workspace, with each coil 141 facing downwards at a 45 degree angle towards the workspace 149. In some embodiments, each coil 141 comprises a solid iron core and 712 wraps of 14 gauge copper wire in 6 layers. The electromagnetic field generation system 104 is calibrated to 27 points comprising 8 "octants" within a 32×32×35 mm3 workspace 149. This calibration accounts for the linear relationships between each coil's magnetic field intensity and the physical positioning of the ferrofluid droplet 102 in the workspace 149, thus allowing each coil 141 to affect the ferrofluid droplet 102 predictably regardless of the location.

Two power supplies are used: a TITAN F1208 capable of providing 60 A and up to 1200 W of electrical power, and an eFueld PSU50A V2 capable of providing 50 A and up to 1200 W of electrical power. Four Sabertooth 2×25 dual motor drivers are used as amplifiers between the power supplies and the coils. Amplifiers are connected to a Sensoray Multifunction analog/digital I/O—Model 826 data acquisition card (DAQ) to receive the controlling inputs. To avoid the adverse impacts of fluctuating temperatures on the magnetic field generation capabilities of the electromagnetic coils, a Fluid Chillers Inc. NEMA 4X Outdoor Enclosure cooling system circulates chilled water through copper tubing that is wound around each coil. While running this cooling setup, system temperatures remain between 21° C. and 24° C.

The workspace 149 is comprised of an open-top cube assembled from matte finished white acrylic square tiles, laser cut for repeatability and assembled via superglue, and a 3D printed white PLA fixture that holds the cube in place and acts as a sliding handle for inserting the cube into the center of the electromagnetic coil system. The cube is filled with 30 ml of 70% isopropyl alcohol; then 5 µL of the ferrofluid is added via micro pipette, forming a droplet.

In the results shown, one ferrofluid (EFH-1) is explored. However, other ferrofluids will likely behave similarly as they all are colloidal suspensions of magnetic particles, regardless of particle size and suspension fluid. There are many types of ferrofluid with different properties, some of which are bio-compatible. EFH-1 ferrofluid is chosen for this study since it is found immiscible in 70% isopropyl alcohol, a commonly available substance. The scalability of ferrofluid droplet size is dependent upon the competing forces acting on it. The surface tension and cohesive forces work to bring the droplet into a spherical shape while magnetic forces attempt to deform it. The surface tension forces act on the surface while magnetic forces are body forces. Thus, the bigger the droplet gets (centimeter scale), the smaller the surface tension becomes compared to the magnetic forces. On the other hand, the surface tension becomes dominant in smaller droplets (micro scale) which forces the droplet into a spherical shape.

One stationary camera 142 provides visual feedback of the workspace 149 from the top. The camera 142 is programmed to capture frames of 276×280 pixels, of which the ferrofluid's range of motion spans a 240×240 pixel region. Resolution is reduced to increase frame rate by reducing image processing computation time. The entire system 100 is controlled through C++ by a single Dell Precision T1700 computer.

Control Scheme

To control the position and shape of the ferrofluid droplet 102 on a predetermined trajectory, the desired path and evolution is segmented into a series of steps which include a point-to-point breakdown of the desired path, required stretch angles, and required stretch lengths, fed to the controller 106 in the form of an array. Each row in the array has four components corresponding to the x position, y position, stretch angle, and stretch length of the next desired pose. The magnetic field and gradient are controlled by PID controllers 161, 162, 163 to steer the ferrofluid droplet 102 towards the next comprehensive pose in the array. As the ferrofluid droplet 102 approaches the desired configuration, and falls within a predefined threshold of accuracy for each of the four metrics, the controller 106 will move on to the next point in the path, methodically moving through each predefined position/shape path.

Feedback Parameter Acquisition

The camera 142 collects one top-view image of the workspace 149 during every iteration of the loop. The ferrofluid droplet 102 appears black against a white background, making it very easy to threshold the image into a binary format. This thresholding process results in a binary image: an array of booleans marking the pixels hosting the ferrofluid droplet 102. From this binary image, the center point of the ferrofluid droplet 102 is obtained by the moments method in the OpenCV image processing library for C++. This method finds the "centroid" of the image by taking a weighted average of the pixel values in the x and y directions and dividing by the area of nonzero pixels. This method is effective for binary images, in particular.

The ferrofluid droplet 102 contours are determined from the binary image using the Canny method in OpenCV for C++. The contours are an array of Cartesian pixel coordinates that describe the outer boundary of the droplet. If multiple contours are detected in the image, all contours are combined into a single array and duplicate pixels in that resulting array are removed. This final array of pixels is used to determine the shape information by the following approach: The stretch angle, θ, is determined by finding the eigenvector that corresponds to the largest eigenvalue of the covariance matrix of all pixels comprising the boundary contour. The angle between this vector and the $x_0$ axis gives θ, as seen in FIG. 1B. The other eigenvector describes the orientation of the minor axis of the ferrofluid droplet 102, and is unused. The stretch length L is determined by finding the maximum distance from any contour pixel to the center point; resulting in a measurement of the major axis radius, as seen in FIG. 1C.

Computer-Implemented System

Figure 11:
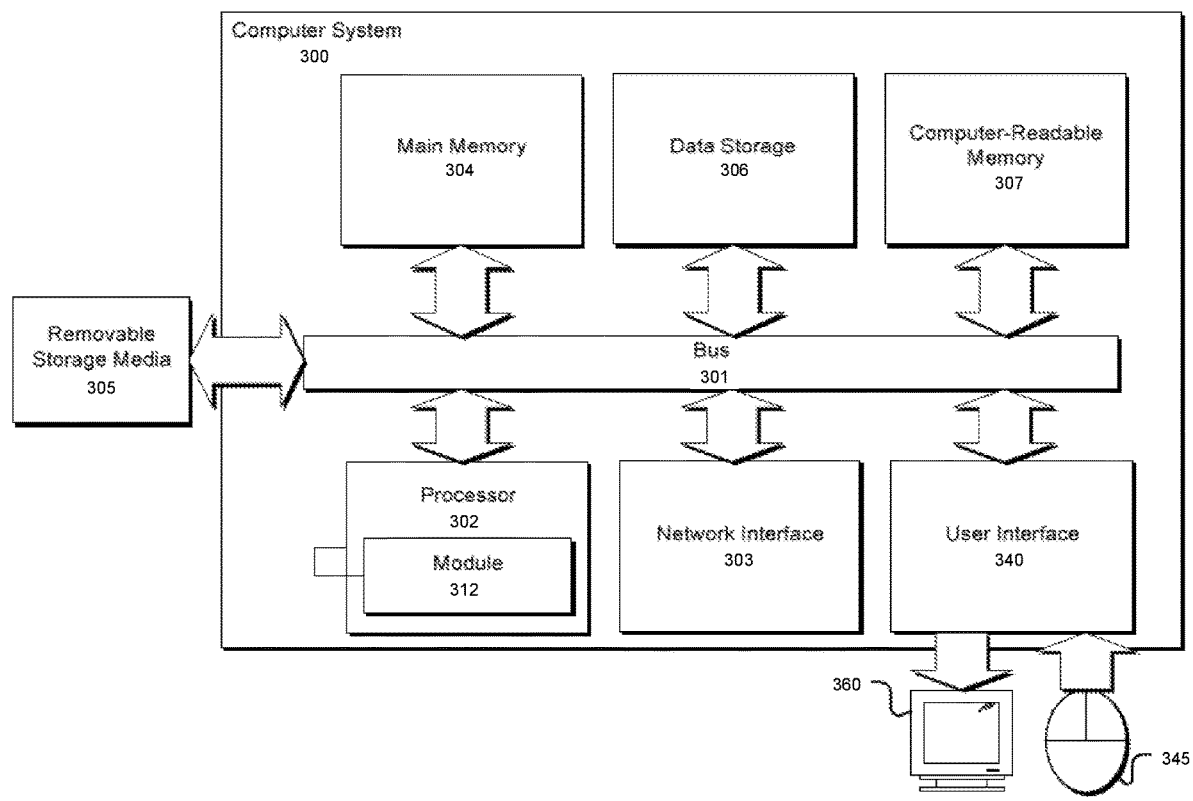
FIG. 11 is an exemplary computing system for use with the system for control of the ferrofluid droplet.

FIG. 11 illustrates an example of a suitable computing and networking environment (computer system 300) which may be used to implement various aspects of the present disclosure. Example embodiments described herein may be implemented at least in part in electronic circuitry; in computer hardware executing firmware and/or software instructions; and/or in combinations thereof. Example embodiments also may be implemented using a computer program product (e.g., a computer program tangibly or non-transitorily embodied in a machine-readable medium and including instructions for execution by, or to control the operation of, a data processing apparatus, such as, for example, one or more programmable processors or computers). A computer program may be written in any form of programming language, including compiled or interpreted languages, and may be deployed in any form, including as a stand-alone program or as a subroutine or other unit suitable for use in a computing environment. Also, a computer program can be deployed to be executed on one computer, or to be executed on multiple computers at one site or distributed across multiple sites and interconnected by a communication network.

Certain embodiments are described herein as including one or more modules. Such modules are hardware-implemented, and thus include at least one tangible unit capable of performing certain operations and may be configured or arranged in a certain manner. For example, a hardware-implemented module may comprise dedicated circuitry that is permanently configured (e.g., as a special-purpose processor, such as a field-programmable gate array (FPGA) or an application-specific integrated circuit (ASIC)) to perform certain operations. A hardware-implemented module may also comprise programmable circuitry (e.g., as encompassed within a general-purpose processor or other programmable processor) that is temporarily configured by software or firmware to perform certain operations. In some example embodiments, one or more computer systems (e.g., a stand-alone system, a client and/or server computer system, or a peer-to-peer computer system) or one or more processors may be configured by software (e.g., an application or application portion) as a hardware-implemented module that operates to perform certain operations as described herein.

Accordingly, the term "hardware-implemented module" encompasses a tangible entity, be that an entity that is physically constructed, permanently configured (e.g., hardwired), or temporarily configured (e.g., programmed) to operate in a certain manner and/or to perform certain operations described herein. Considering embodiments in which hardware-implemented modules are temporarily configured (e.g., programmed), each of the hardware-implemented modules need not be configured or instantiated at any one instance in time. For example, where the hardware-implemented modules comprise a general-purpose processor configured using software, the general-purpose processor may be configured as respective different hardware-implemented modules at different times. Software, in the form of the system applications 100/200 or otherwise, may include a hardware-implemented module and may accordingly configure a processor 302, for example, to constitute a particular hardware-implemented module at one instance of time and to constitute a different hardware-implemented module at a different instance of time.

Hardware-implemented modules may provide information to, and/or receive information from, other hardware-implemented modules. Accordingly, the described hardware-implemented modules may be regarded as being communicatively coupled. Where multiple of such hardware-implemented modules exist contemporaneously, communications may be achieved through signal transmission (e.g., over appropriate circuits and buses) that connect the hardware-implemented modules. In embodiments in which multiple hardware-implemented modules are configured or instantiated at different times, communications between such hardware-implemented modules may be achieved, for example, through the storage and retrieval of information in memory structures to which the multiple hardware-implemented modules have access. For example, one hardware-implemented module may perform an operation, and may store the output of that operation in a memory device to which it is communicatively coupled. A further hardware-implemented module may then, at a later time, access the memory device to retrieve and process the stored output. Hardware-implemented modules may also initiate communications with input or output devices.

As illustrated, the computing and networking environment 300 may be a general purpose computing device 300, although it is contemplated that the networking environment 300 may include other computing systems, such as personal computers, server computers, hand-held or laptop devices, tablet devices, multiprocessor systems, microprocessor-based systems, set top boxes, programmable consumer electronic devices, network PCs, minicomputers, mainframe computers, digital signal processors, state machines, logic circuitries, distributed computing environments that include any of the above computing systems or devices, and the like.

Components of the general purpose computing device 300 may include various hardware components, such as a processing unit 302, a main memory 304 (e.g., a system memory), and a system bus 301 that couples various system components of the general purpose computing device 300 to the processing unit 302. The system bus 301 may be any of several types of bus structures including a memory bus or memory controller, a peripheral bus, and a local bus using any of a variety of bus architectures. For example, such architectures may include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

The general purpose computing device 300 may further include a variety of computer-readable media 307 that includes removable/non-removable media and volatile/non-volatile media, but excludes transitory propagated signals. Computer-readable media 307 may also include computer storage media and communication media. Computer storage media includes removable/non-removable media and volatile/nonvolatile media implemented in any method or technology for storage of information, such as computer-readable instructions, data structures, program modules or other data, such as RAM, ROM, EPSOM, flash memory or other memory technology, CD-ROM, digital versatile disks (DVD) or other optical disk storage, magnetic cassettes, magnetic tape, magnetic disk storage or other magnetic storage devices, or any other medium that may be used to store the desired information/data and which may be accessed by the general purpose computing device 300. Communication media includes computer-readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. For example, communication media may include wired media such as a wired network or direct-wired connection and wireless media such as acoustic, RF, infrared, and/or other wireless media, or some combination thereof. Computer-readable media may be embodied as a computer program product, such as software stored on computer storage media.

The main memory 304 includes computer storage media in the form of volatile/nonvolatile memory such as read-only memory (ROM) and random access memory (RAM). A basic input/output system (BIOS), containing the basic routines that help to transfer information between elements within the general purpose computing device 300 (e.g., during start-up) is typically stored in ROM. RAM typically contains data and/or program modules that are immediately accessible to and/or presently being operated on by processing unit 302. For example, in one embodiment, data storage 306 holds an operating system, application programs, and other program modules and program data.

Data storage 306 may also include other removable/non-removable, volatile/nonvolatile computer storage media. For example, data storage 306 may be: a hard disk drive that reads from or writes to non-removable, nonvolatile magnetic media; a magnetic disk drive that reads from or writes to a removable, nonvolatile magnetic disk; and/or an optical disk drive that reads from or writes to a removable, nonvolatile optical disk such as a CD-ROM or other optical media. Other removable/non-removable, volatile/nonvolatile computer storage media may include magnetic tape cassettes, flash memory cards, digital versatile disks, digital video tape, solid state RAM, solid state ROM, and the like. The drives and their associated computer storage media provide storage of computer-readable instructions, data structures, program modules and other data for the general purpose computing device 200.

A user may enter commands and information through a user interface 340 or other input devices 345 such as a tablet, electronic digitizer, a microphone, keyboard, and/or pointing device, commonly referred to as mouse, trackball, or touch pad. Other input devices 345 may include a joystick, game pad, satellite dish, scanner, or the like. Additionally, voice inputs, gesture inputs (e.g., via hands or fingers), or other natural user interfaces may also be used with the appropriate input devices, such as a microphone, camera 350, tablet, touch pad, glove, or other sensor. These and other input devices 345 are often connected to the processing unit 302 through a user interface 340 that is coupled to the system bus 301, but may be connected by other interface and bus structures, such as a parallel port, game port or a universal serial bus (USB). A monitor 360 or other type of display device is also connected to the system bus 301 via user interface 340, such as a video interface. The monitor 360 may also be integrated with a touch-screen panel or the like.

The general purpose computing device 300 may operate in a networked or cloud-computing environment using logical connections of a network Interface 303 to one or more remote devices, such as a remote computer. The remote computer may be a personal computer, a server, a router, a network PC, a peer device or other common network node, and typically includes many or all of the elements described above relative to the general purpose computing device 300. The logical connection may include one or more local area networks (LAN) and one or more wide area networks (WAN), but may also include other networks. Such networking environments are commonplace in offices, enterprise-wide computer networks, intranets and the Internet.

When used in a networked or cloud-computing environment, the general purpose computing device 300 may be connected to a public and/or private network through the network interface 303. In such embodiments, a modem or other means for establishing communications over the network is connected to the system bus 301 via the network interface 303 or other appropriate mechanism. A wireless networking component including an interface and antenna may be coupled through a suitable device such as an access point or peer computer to a network. In a networked environment, program modules depicted relative to the general purpose computing device 300, or portions thereof, may be stored in the remote memory storage device.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A system for the control of a ferrofluid droplet, the system comprising:
    a ferrofluid droplet; and
    an electromagnetic field generation system, comprising:
        a plurality of electromagnetic coils, the plurality of electromagnetic coils being operable to generate a magnetic field when an electric current is applied to each of the plurality of coils;
    a controller in operative communication with the electromagnetic field generation system and operable for storing instructions, which,
        when executed, cause the controller to:
            determine an instant position, an instant stretch angle and an instant stretch length of the ferrofluid droplet;
            identify a position difference between instant position and a target position;
            identify a stretch angle difference between instant stretch angle and a target stretch angle;
            identify a stretch length difference between an instant stretch length and a target stretch length;
            determine a magnetic field magnitude necessary to manipulate the ferrofluid droplet into the target stretch length from the instant stretch length;
            determine a magnetic field angle necessary to manipulate the ferrofluid droplet into the target stretch angle from the instant stretch angle;
            determine a force vector necessary to manipulate the ferrofluid droplet into the target position from the instant position; and
            determine a set of electric currents, wherein each electric current of the set of electric currents is applied to one of the plurality of coils of the electromagnetic field generation system such that the electromagnetic field generation system applies the magnetic field magnitude, the magnetic field angle and the force vector to the ferrofluid droplet.

2. The system of claim 1, further comprising:
    a camera in communication with the controller, wherein the camera provides an image of the ferrofluid droplet to the controller.

3. The system of claim 2, wherein the controller is operable to determine the instant position, the instant stretch angle, and the instant stretch length of the ferrofluid droplet using the image captured from the camera by an image processing module.

4. The system of claim 1, wherein one or more of the plurality of electromagnetic coils are arranged horizontally along a horizontal plane and wherein one or more of the plurality of electromagnetic coils are arranged at a predetermined angle relative to the horizontal plane.

5. The system of claim 1, wherein the controller comprises:
a position controller operable to determine the force vector, wherein the force vector manipulates a position of the ferrofluid droplet in an XY plane.

6. The system of claim 5, wherein the position controller comprises:
a first position controller operable to determine the force vector necessary to manipulate the ferrofluid droplet into the target position from the instant position relative to an X axis, wherein the first position controller is a proportional-integral-derivative controller.

7. The system of claim 5, wherein the position controller comprises:
a second position controller operable to determine the force vector necessary to manipulate the ferrofluid droplet into the target position from the instant position relative to a Y axis, wherein the second position controller is a proportional-integral-derivative controller.

8. The system of claim 1, wherein the controller comprises:
a stretch length controller operable to determine the magnetic field magnitude necessary to manipulate the ferrofluid droplet into the target stretch length from the instant stretch length, wherein the stretch length position controller is a proportional-integral-derivative controller.

9. The system of claim 1, wherein the controller comprises:
a stretch angle controller operable to determine the magnetic field angle necessary to manipulate the ferrofluid droplet into the target stretch angle from the instant stretch angle, wherein the stretch angle controller is a proportional-integral-derivative controller.

10. The system of claim 1, wherein the controller comprises:
a current determination module, the current determination module being operable to identify the set of electric currents such that the magnetic field generated by the plurality of electromagnetic coils based on the magnetic field stretch angle, magnetic field magnitude, and force vector as determined by the controller, wherein each electric current of the set of electric currents is applied to a respective electromagnetic coil of the plurality of electromagnetic coils.

11. A method for controlling a ferrofluidic droplet, comprising:
determining, by processor, an instant position, an instant stretch angle and an instant stretch length of a ferrofluid droplet;
identifying, by processor, a position difference between instant position and a target position;
identifying, by processor, a stretch angle difference between instant stretch angle and a target stretch angle;
identifying, by processor, a stretch length difference between an instant stretch length and a target stretch length;
determining, by processor, a magnetic field magnitude necessary to manipulate the ferrofluid droplet into the target stretch length from the instant stretch length;
determining, by processor, a magnetic field angle necessary to manipulate the ferrofluid droplet into the target stretch angle from the instant stretch angle;
determining, by processor, a force vector necessary to manipulate the ferrofluid droplet into the target position from the instant position; and
determining, by processor, a set of electric currents, wherein each electric current of the set of electric currents is applied to one of a plurality of coils of an electromagnetic field generation system such that the electromagnetic field generation system applies the magnetic field magnitude, the magnetic field angle and the force vector to the ferrofluid droplet.

12. The method of claim 11, wherein the controller is operable to determine the instant position, the instant stretch angle, and the instant stretch length of the ferrofluid droplet using an image provided by a camera.

13. The method of claim 11, wherein the controller is operable to determine the force vector by a position controller using the position difference between an instant position and a target position, wherein the force vector manipulates the position of the ferrofluid droplet in an XY plane.

14. The method of claim 13, wherein the position controller determines the force vector using a relation:

$$F = \begin{bmatrix} F_x \\ F_y \end{bmatrix} = K_{PP}E_P + K_{DP}\dot{E}_P + K_{IP}\int E_P dt,$$

wherein $E_P$ is the position difference between the instant position and the target position, $K_{PP}$ is a constant representing proportional gain, $K_{DP}$ is a constant representing derivative gain, and $K_{IP}$ is a constant representing integral gain of the position controller.

15. The method of claim 11, wherein the controller is operable to determine the magnetic field angle by a stretch angle controller using stretch angle difference between an instant stretch angle and a target stretch angle, wherein the magnetic field angle manipulates the stretch angle of the ferrofluid droplet.

16. The method of claim 15, wherein the stretch angle controller determines the magnetic field angle using a relation: $\theta_B = K_{P\theta}e_\theta + K_{D\theta}\dot{e}_\theta + K_{I\theta}\int e_\theta dt$, wherein $e_\theta$ is the stretch angle difference between the instant stretch angle and the target stretch angle, $K_{P\theta}$ is a positive constant representing proportional gain, $K_{I\theta}$ is a positive constant representing integral gain, and $K_{D\theta}$ is a positive constant representing derivative gain of the stretch angle controller.

17. The method of claim 11, wherein the controller is operable to determine the magnetic field magnitude by a stretch length controller using a stretch length difference between an instant stretch length and a target stretch length, wherein the magnetic field magnitude manipulates the stretch length of the ferrofluid droplet.

18. The method of claim 17, wherein the stretch length controller determines the magnetic field magnitude using a relation:
$L_B = K_{PL}e_L + K_{DL}\dot{e}_L + K_{IL}\int e_L dt$ wherein $e_L$ is the stretch length difference between the instant stretch length and the target stretch length, $K_{PL}$ is a positive constant representing proportional gain, $K_{IL}$ is a positive constant representing integral gain, and $K_{DL}$ is a positive constant representing derivative gain of the stretch length controller.

19. The method of claim 11, wherein the method is iteratively repeated until the instant position, the instant stretch angle, and the instant stretch length of a ferrofluid droplet are at the target position, the target stretch angle, and the target stretch length.

20. The method of claim 11, further comprising:
producing a short pulse of the magnetic field at a specified stretch angle and at a high stretch length such that the ferrofluid droplet is caused to split into two ferrofluid droplets.

21. The method of claim 11, further comprising:
generating the magnetic field at a specified stretch angle and at a low stretch length such that two ferrofluid droplets are caused to combine into one ferrofluid droplet.

* * * * *